(12) United States Patent
Liebergesell et al.

(10) Patent No.: US 6,515,205 B1
(45) Date of Patent: Feb. 4, 2003

(54) **GENES FROM *CHROMATIUM VINOSUM* FOR THE PRODUCTION OF POLYHYDROXYALKANOATE**

(76) Inventors: Matthias Liebergesell, Institut für Mikrobiologie, Georg-August-Unversität, Grisebachstrasse 8, 3400 Göttingen (DE); Alexander Steinbuchel, Institut für Mikrobiologie, Georg-August-Universität, Grisebachstrasse 8, 3400 Göttingen (DE)

( * ) Notice: Subject to any disclaimer, the term of this patent is extended or adjusted under 35 U.S.C. 154(b) by 0 days.

(21) Appl. No.: 08/178,257

(22) PCT Filed: Jul. 15, 1992

(86) PCT No.: PCT/GB92/01291
§ 371 (c)(1),
(2), (4) Date: May 6, 1994

(87) PCT Pub. No.: WO93/01291
PCT Pub. Date: Feb. 4, 1993

(30) Foreign Application Priority Data

Jul. 16, 1991 (GB) .............................................. 9115245

(51) Int. Cl.⁷ .......................... C12N 15/82; C12N 1/20; A01H 5/00; C07H 21/04
(52) U.S. Cl. ...................... 800/288; 800/298; 435/69.1; 435/320.1; 435/419; 435/471; 435/252.3; 536/23.2
(58) Field of Search ................................ 800/288, 298; 536/23.2; 435/69.1, 320.1, 419, 468, 471, 272.3

(56) References Cited

FOREIGN PATENT DOCUMENTS

| | | |
|---|---|---|
| WO | 8900202 | 1/1989 |
| WO | 9100917 | 1/1991 |

OTHER PUBLICATIONS

Perlak et al (1991) Proc. Natl. Acad Sci USA 88:3324–3328.*
Finnegan et al (1994) Bio/Technology 12:883–888.*
Archives of Microbiology, vol. 155, No. 5, 1991, pp. 415–421, Liebergesell, et al: 'Formation of ploy–33 hydroxyalkanoates by phototrophic and chemolithic bacteria', see the whole document.
Trends in Biotechnology, vol. 5, No. 9, Sep. 1997, pp. 246–250, BYROM, D.: 'Polymer synthesis by microorganisma: technology and economics', see p. 248, left col.; table 2.
Journal of Biological Chemistry, vol. 264, No. 26, Sep. 15, 1989, pp. 15298–15303, Peoples, et al: 'Poly–beta–hydroxybutyrate (PHB) biosynthesis in *Alcaligenes eutrophus* H16', see figure 4.
Journal of Biological Chemistry, vol. 264, No. 26, Sep. 15, 1989, pp. 15293–15297, Peoples, et al: 'Poly–beta–hydroxybutyrate biosynthesis in *Alcaligenes eutrophus* H16', see figures 5, 6.
Science, vol. 245, Sep. 15, 1989, pp. 1187–1189, Pool, et al:'In search of the plastic potato', pg. 1189, col. 2–.
J. Bacteriology, vol. 170, No. 12, Dec. 1988, pp. 5837–5847, Schubert et al: 'Cloning of the *alcaligenes eutrophus* genes for synthesis of PHB in *Escherichia coli*' see the whole document.

* cited by examiner

*Primary Examiner*—Elizabeth F. McElwain

(57) ABSTRACT

Genes encoding polyhydroxyalkanoate synthase, β-ketothiolase and acetoacetyl CoA reductase are isolated from the publicly available bacterium *Chromatium vinosum*. Recombinant genomes of plants or other species of bacteria which contain these genes are capable of producing polyalkanoate polymers. The nucleotide sequences of the said three geneés have been determined.

15 Claims, 46 Drawing Sheets

AAGCTAAAGGTCTGGGACAGTGTACTTTGGGCTATCAGACGAGTACTCATG

CGCGGCCTACAGCTAAACAACTAGCTTCCTGACTCGGCCGGACCTAAGGAC

GGAAACGCTGACCGCGGCCGAAGGACTCAGATGACTGGAAACGGCCGACGC

GTAGGGCGGTCAGTCAGTCGTAGGTTCCAACTACCAACCGGCATTGTGCGC

GACCACCTTGTGACCCGGTGCGTAGGCGTACGGCCGCACGTTACAGGCCGG

CTAAGCCTGCGCGGAAGCACGTCTAGCTTCTCCAGAAAGGCCCACTCCGTC

GACCGCTGTAAAGATGTAGGTCCTAACTTAGTTCGGACCATATCCCCGCGG

ACTCAGGGCTCGCAGTAGCACCTACGGCAAGCTGCCGACTGCTGTCGCTCG

GAATGGCTACCGGCCGCACTGAAGAAAGACGCGGAACGGCGACTGTATCTA
 K  G  I  A  P  T  V  E  K  Q  A  K  G  S  V  Y  I

CAGTCAGGGAACTCGCGGGATCTCCGTAGGCCGCCGTGGTCCACTAGGACC
 T  L  G  K  L  A  R  S  A  D  P  P  V  L  H  D  Q

GGACAGGCGGGTCGTGGTGCGGCGGTAACTCCTTCGGCAACAAGACCATCT
 E  Q  G  G  L  V  V  G  G  N  L  F  G  N  N  Q  Y

FIG. 3B

```
1101  TCAGGAACTACTTGACTGCCTTCCAGAGCGGCCGGACTAGGCCCGACA
      F  D  K  I  F  Q  R  F  T  E  G  A  Q  D  P  S

1201  CTCGTCTAGTTGGTACAACTGCATGAAGACTGGGCAGTCCGACTTTCC
       L  L  D  V  M  N  V  Y  K  Q  G  T  L  S  F  P

1301  CACAGCTGGCGGTCTAGCTACAGCTGCAAGACGTGGGTCCGGCTCTCG
       T  D  V  A  L  D  I  D  V  N  Q  V  W  A  S  L

1401  CGTGGAACAGGCCCACGTCGCGCGACATGTAGTCCGACTTCCGCGGCG
       R  V  K  D  P  H  L  A  S  Y  M  L  S  F  A  G

1501  TATCAGGTGCGTCGCCAGCTACATCGGCAACTACATCAGCAGCTCGCA
       Y  D  V  C  R  D  I  Y  G  N  I  Y  D  D  L  T

1601  ACCGGCCACCGGTCGTCAGGGAACTACCACCTCGCCAGAAGGACCTAC
       Q  G  T  A  L  L  G  K  I  T  S  R  D  E  Q  I

1701  CGACCCGAAGCCCGCGCGGGAGCCCAGCCAGTATCGCTATCTCCTGGT
       P  Q  A  E  P  A  G  E  P  R  D  Y  R  Y  L  V

1801  GAGCCGCAACTCGTCTAAGAGGTACGGGACTGGGTCGAACGCCGACAT
       E  A  N  L  L  N  E  M  G  Q  G  L  K  R  S  Y

S/D
1901  TAGCGACAGGAGACTAAGACAGACCACTCGGACGACAAGCTAGTCGGC

2001  GGAACCGCCGGCCCCGCCCGCTGGACTCGCGTCACCGTCCGAACCACC
       A  K  A  A  P  A  P  S  R  L  A  T  A  P  K  T
```

FIG. 3C

```
GCTTCTAGGTAAAGAGGTACGCGTCCTTCAAGAACTGGAACAGGCCCAGCAG
 P  F  I  W  K  E  M  R  L  F  N  K  V  K  D  P  D  D

GAACTCGCTGTCCTTCCAGGTCAAGTCGTCGAGTGGCCCCTACAACGGGTAC
  K  L  S  L  F  T  W  N  L  L  E  G  P  I  N  G  M

TCCAACAGGCCCCAGAACTTCAGCTGGCCGCACTGGTACCAGTGCTCCAACG
 L  N  D  P  T  K  F  D  V  P  T  V  M  T  V  L  N

GGACTGTCTATGGCTCGTCTAACTGGAACAGCTGCGGCACCCGAAGCGCGTC
 G  Q  C  I  G  L  L  N  V  K  D  V  G  H  A  E  R  L

CTCGCGCGCCAGCGGGACTAGGCCTATCGGGGTCAGCTAGTCCATCTGCAGG
  L  A  R  D  A  Q  D  P  Y  G  W  D  I  L  Y  V  D

AGCCAGTACATCCCGGCCAACTGGTCCCGCATCTGCTAGTCCTCGCCGTGCC
  D  T  M  Y  P  R  N  V  L  A  Y  V  I  L  L  P  V

CGAACAGGAGCGACATCTGCCGGACGAACCCCGACTGCGGCCACAGCTACCG
 L  K  D  E  S  Y  V  A  Q  K  P  S  V  G  T  D  I  A

←―――― ORF3
CAGCTCGTAGAGGACCCACTCAAACAGGCCGGCCTACAGCTACCCCTTGTAC
 D  L  M  E  Q  T  L  K  D  P  R  I  D  I  P  F  M

GAACTGCGAGTTAGCCGGCCTAACCAGAACCACCACGCGGCCGCACGGCCTC
        *  D  A  P  N  T  K  T  T  R  R  A  P

GGCCGAGGAGTGGCCGGTCCCGACGCTGCGCTGCAAGGTCTAGCGCGTCCGA
 A  P  E  E  G  A  L  A  A  V  R  R  E  L  D  R  L  S
```

FIG. 3D

```
2101  CACTGCGTCCCGGAACAAGAGCGCTGCCCAGAGGACCTCGGCCAGGACC
       H  R  L  A  K  N  E  R  R  T  E  Q  L  R  D  Q

2201  AGCTGGTCCTAGCTGTACGCGAAGAACTCGCGGTAGACTCGCAACTGGT
       D  V  L  I  S  M  R  K  K  L  A  M  Q  A  N  V

2301  GCGGAAGCGTCGTCCGCTGGGTCAACAGCATCTCGCGCGCGCGGCTCAG
       A  G  E  C  C  A  V  W  N  D  Y  L  A  R  A  S  D

2401  CTGGCTGAAGTACGGCTCGAACCACATCTGCAACCACATAAGGACCTCG
       V  S  K  M  G  L  K  T  Y  V  N  T  Y  E  Q  L

2501  AGGAGCGCCCACATCGGCTCTGGCCCGCGGCTCTCCCGAGCTAGTTCTG
       E  E  R  T  Y  G  L  G  P  A  S  L  A  R  D  L

2601  CGCTGTAGCTCCTGTAGTACGCGACGGTCAACAGCTCGCCGTCGAGGGT
       P  S  M  S  S  M  M  R  Q  W  N  D  L  P  L  E  W

2701  CTTCGCGAAGACGTACAGAAGCTCGCAGAACCAGGTCTCGAGGTTCGGC
       F  R  K  Q  M  D  E  L  T  K  T  W  L  E  L  G

2801  TTCTTCAAGAACGGGACGAGGTAGTAGAAAAGGTACTTGCTCGCACTGT
       F  F  N  K  G  Q  E  M  M  K  E  M  F  S  R  S

2901  GGGTCCCGCACAACCGGCTTGACCTCCGCGACAGGTCTGGGTACCGGAA
       E  W  P  T  T  A  S  S  S  A  S  D  L  G  M  A  K

←ORF2      S/D
3001  TAGCAGTAACTTCTTTAATCACAACGAGTACCTGCATGGGAGGAGCACC
       D  D  N  F  F  N  T  N  S  M
```

FIG. 3E

```
TCCCACGCGTCGAGCGACGCCCAGCCGTACAAGTTACGCGGGTCCAAGAGC
 L  T  P  L  E  S  R  T  P  M  N  L  A  G  L  N  E

CGGCCGGCACCTACGCCCGCATAAGGCCACACCGCTGGAGCAGCCGTATCC
 L  R  G  H  I  R  A  Y  E  P  T  A  V  E  D  A  Y

CTACCAAAACGGCGACAGCTACTGTGGGACCTACATCCTCGGGTACACGAG
  I  T  K  G  S  D  I  V  G  Q  I  Y  S  G  M  H  E

CGCCGGACTATGAGGTACCGCGACGCGTAGTCGAGGACTATGACCGAGACG
 A  A  Q  Y  E  M  A  S  R  M  L  E  Q  Y  Q  S  Q

ACAGGAACTTGACGAGCACCCCGTACAACGCGTCGTACAGCGGGCCGTAGC
 S  D  K  F  Q  E  H  P  M  N  R  L  M  D  G  P  M

CTTGCTGTAGTCCGCGACGTACCACAACGGCGGCAGCAGCTCGCTCGGCGA
 F  S  M  L  R  Q  M  T  N  G  G  D  D  L  S  G  S

AACGGCCGCAACGGGAGCAGCCGCGCAAACCGCTTCCACAGCCGCTCTGCC
  N  G  A  N  G  E  D  A  R  K  A  F  T  D  A  L  R

CTAGGCCCCGCCGCCCGCGGGTACCGAAAGGTGGTGACTAGCTACCGGCGGA
 L  D  P  A  A  P  A  M  A  K  W  W  Q  D  I  A  A

CGCCGAGTACAGCCAGGTCAACAGGGTCATGAACGCAACGTCAAGCTCGGT
 R  S  M  D  T  W  N  D  W  Y  K  R  Q  L  E  L  W
```

←mRNA　　　　　　　　　　　"-35" Ketothiolase
GCGCACCACAACCCGCTTGCCATAGTACACCTAAACACGTGACGTTGTTTC
　　　　　"-10"　　　　ORF2　　　　　"-35"

FIG. 3F

```
                    "-10"
3101  TACGCATCTTAGGTGTCCGGCGCTGGGGTATAGCCCCTGCGAGCAGGTA

V  D  A  G  R  S  A  I  G  T  F  G  G  S  L  S
3201  GCAGCTGCGGCCGGCGTCACGGTAGCCTTGGAAGCCGCCGTCAGACAGC

R  T  G  L  A  P  E  Q  I  D  E  V  I  L  G  Q  V
3301  GCATGGCCTGAGCGCGGCCTTGTCTAGCTGCTCCACTAAGAGCCGGTCC

G  L  P  H  S  V  P  A  M  T  I  N  K  V  C  G
3401  GCCCCGATGGCGTAAGCCACGGCCGGTACTGGTAGTTGTTCCAGACGCC

A  D  I  V  I  A  G  G  Q  E  S  M  S  Q  S  S
3501  ACGGCTGTAGCAGTAGCGGCCGCCAGTCCTCTCGTACTCGGTCAGGAGC

K  D  T  M  I  V  D  G  L  W  D  A  F  N  N  Y  H
3601  TTCCTGTGGTACTAGCAGCTGCCGGAGACCCTACGGAAGTTGTTGATAG

Q  Q  D  A  F  A  A  A  S  Q  Q  K  T  E  A  A
3701  TCGTCGTCCTGCGGAAGCGGCGGCGGAGCGTCGTCTTCTGGCTCCGGCG

R  K  G  D  P  K  V  F  D  A  D  E  F  P  R  H
3801  CGCGTTCCCGCTAGGCTTCCACAAACTACGGCTGCTCAAGGGCGCAGTG

G  S  V  T  A  G  N  A  S  G  I  N  D  G  A  A  M
3901  CCGTCGCAGTGCCGCCCATTGCGGAGGCCGTAGTTGCTGCCCCGCCGGT

A  R  L  V  A  F  A  S  A  G  V  D  P  A  I  M
4001  ACCGCGCAGACCACCGGAAGCGGTCGCGGCCACAGCTAGGCCGCTAGTA
```

FIG. 3G

```
                                                        Ketothiolase
                    S/D              M  S  E  N  I  V  I
AAGGTTAGTCTTAGGTCTCCTGTAGGTGCGGTACTCGCTCTTGTAGCAGTA S  L  S  A  T  E  I  G  T  A  V  L  K  G  L  L  A
AGTGAGAGCCGGTGGCTCTAGCCGTGGCGGCACGAGTTCCCCGACGACCGC L  T  A  G  V  G  Q  N  P  A  R  Q  T  T  L  H  A
ACGACTGGCGGCCGCACCCGGTCTTGGGGCGGGCAGTCTGGTGCGACGTGC S  G  L  K  A  V  H  L  A  M  Q  A  I  A  C  G  D
GTCGCCAGACTTCCGCCACGTAGACCGCTACGTCCGGTAGCGGACGCCCCT H  V  L  P  R  S  R  D  G  Q  R  M  G  D  W  S  M
GTGCAGGACGGCGCAAGCGCGCTGCCAGTCGCGTACCCGCTGACCAGCTAC M  G  T  T  A  E  N  I  A  Q  K  Y  G  F  T  R  E
TGTACCCGTGGTGGCGGCTCTTGTAGCGGGTCTTCATGCCGAAATGCGCGC Q  K  A  G  R  F  Q  D  E  I  I  P  I  E  I  P  Q
CGTCTTCCGACCGGCGAAGGTCCTGCTCTAGTAAGGCTAGCTCTAAGGCGT G  T  T  A  E  S  L  G  K  L  R  P  A  F  S  K  D
CCGTGGTGCCGGCTCTCAGACCCGTTCGACGCAGGCCGGAAGAGCTTCCTG V  V  V  M  K  E  S  K  A  K  E  L  G  L  K  P  M
ACCAGCACCACTACTTCCTCAGGTTCCGGTTCCTTGACCCAGACTTCGGCT G  T  G  P  I  P  A  S  T  K  C  L  E  K  A  G  W
CCCCTGCCCGGGCTAGGGCCGCAGCTGGTTCACGGACCTCTTCCGGCCGAC
```

FIG. 3H

```
           T  P  A  D  L  D  L  I  E  A  N  E  A  F  A  A
4101   CTGGGGCCGCCTAGACCTAGACTAGCTCCGGTTGCTTCGGAAGCGGCGC

V  N  G  G  A  I  A  I  G  H  P  I  G  A  S  G  A
4201   CAGTTGCCGCCGCGGTAGCGGTAGCCAGTAGGCTAGCCGCGGAGGCCAC

G  L  A  T  L  C  I  G  G  G  Q  G  V  A  L  A
4301   TCCCAGACCGCTGCGACACGTAGCCGCCGCCGGTCCCGCACCGCGACCG

4401   TCGGAGGACTTAGCGAGGTCCGTGACTTGCGGGACGGCTAGGGCCTAGC

*Sma* I
4501   GGGCCC
```

```
  Q  A  M  S  V  N  Q  D  M  G  W  D  L  S  K  V  N
GTCCGGTACAGCCAGTTGGTCCTGTACCCGACCCTAGACAGGTTCCAGTTG

R  V  L  V  T  L  L  Y  E  M  Q  K  R  D  A  K  K
GCGCGCACGAGCACTGGGACGAGATACTCTACGTCTTCGCGCTGCGGTTCT

V  E  R  M  *
CCAGCTCGCCTACACTCGGCAGCAGGCGGCCAGACTTAGCGGCCGCCTGGC

CACCCCGCAAACGCGCGAACCCCATCTGAACGGCTTGCTGGTCGGCTTGGC
```

FIG. 31

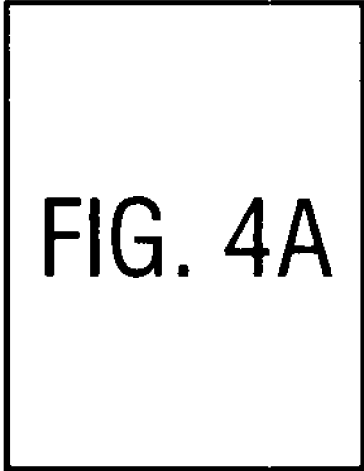
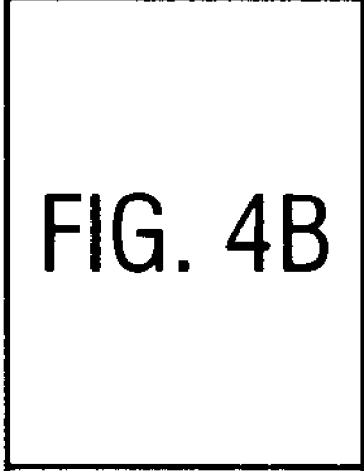
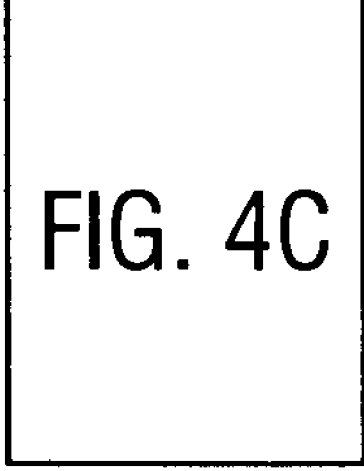
FIG. 4

```
PHB polymerase     173    ESGGESLRAGVRNMMEDLTR--GKISQTDESAFEV-
ORF 3                1    MFPIDIRPDKLTQEMLDYSR---KLGQGMENLLNAE
PHA polymerase 1   149    ETGGKSLLDGLSNLAKDLVNNGGMPSQVNMDAFEV-
PHA polymerase 2   149    NSGGQSLVFGVAHLLDDLRHNDGLPRQVDERAFEV- PHB polymerase     206    GRNVAVTEGAVVFENEYFQLLQYKPLTD--KVHARP
ORF 3               34    AIDTGVSPKQAVYSEDKLVLYRYDRPEGAPEAQPVP
PHA polymerase 1   184    GKNLGTSEGAVVYRNDVLELIQYKPITE--QVHARP
PHA polymerase 2   184    GGNLAATAGAVVFRNELLELIQYKRMSE--KQHARP PHB polymerase     240    LLMVPPCINKYYILDLQPESSLVRHVVEQGHTVFLV
ORF 3               70    LLIVYALVNRPYMTDIQEDRSTIKGLLATGYDVYLI
PHA polymerase 1   218    LLIVPPQINKFYVFDLSPEKSLARYCLRSQQQTFII
PHA polymerase 2   218    LLVVPPQINKFYIFDLSSTNSFVQYMLKNGLQVFMV PHB polymerase     276    SWRNPDASMAGSTWDDYIEHAAIRAIEVARDISGQD
ORF3               106    DWGYPDQADRALTLDDYINGYIDRCVDYLREAHGVD
PHA polymerase 1   254    SWRNPTKAQREWGLSTYID-ALKEAVDAVLAITGSK
PHA polymerase 2   254    SWRNPDPRHREWGLSSYVQ-ALEEALNACRSISGNR
```

FIG. 4A

```
PHB polymerase    312  KINVLGFCVGGTIVSTALAVLAARGE-HPAASVTLL
ORF3              142  KVNLLGICQGGAF---SLMYSALHPD-KVRNLVTMV
PHA polymerase 1  288  DLNMLGACSGGITCTALVGHYAALGE-NKVNALTLL
PHA polymerase 2  288  DPNLMGACAGGLTMAALQGHLQAKHQLRRVRSATYL PHB polymerase    347  TTLLDF-ADTGILDVFVDEGHVQLREATLGGGAGAP
ORF3              174  TP-VDFKTPDNLLSAWVQNVDIDLAVDTMGNIPGE-
PHA polymerase 1  323  VSVLDT-TMDNQVALFVDEQTLEA-----AKRHSYQ
PHA polymerase 2  324  VSLLDS-KFESPASLFADEQTIEA-----AKRRSYQ PHB polymerase    382  CALLRGLELANTFSFLRPNDLVWNYVVDNYLKGNTP
ORF3              208  -LLNWTFLSLKPFSLTGQKYVNMVDLLDDPDKVKNF
PHA polymerase 1  353  AGVLEGSEMAKVFAWMRPNDLIWNYWVNNYLLGNEP
PHA polymerase 2  354  RGVLDGAEVARIFAWMRPNDLIWNYWVNNYLLGKTP PHB polymerase    418  VPFDLLFWNGDATNLPGPWYCWYLRHTYLQNELKVP
ORF3              243  LRMEK--WIFDSPDQAGETFRQFIKDFYQNNGF-LN
PHA polymerase 1  389  PVFDILFWNNDTTRLPAAFHG-DLIEMFKSNPLTRP
PHA polymerase 2  390  PAFDILYWNADSTRLPAALHG-DLLDFFKLNPLTHP
```

FIG. 4B

```
PHB polymerase      454   GKLTVCGVPVDLASIDVPTYIYGSREDHIVPWTAAY
ORF3                276   GGVVLGGQEVDLKDITCPVLNIFALQDHLVPPDASR
PHA polymerase 1    424   DALEVCGTPIDLKQVKCDIYSLAGTNDHITPWQSCY
PHA polymerase 2    425   AGLEVCGTPIDLQKVELDSFTVAGSNDHITPWDAVY PHB polymerase      490   ASTALLAN----KLRFVLGASG-HIAGVINPPAKNK
ORF3                312   ALKGLTSSPDYTELAFPGGHIGIYVSGKAQKEVTPA
PHA polymerase 1    460   RSAHLFGG----KIEFVLSNSG-HIQSILNPPGNPK
PHA polymerase 2    461   RSALLLGG----DRRFVLANSG-HIQSIINPPGNPK PHB polymerase      521   RSHWTNDA
ORF3                348   IGKWLNER
PHA polymerase 1    491   ARFMTGAD
PHA polymerase 1    492   AYYLANPK
```

FIG. 4C

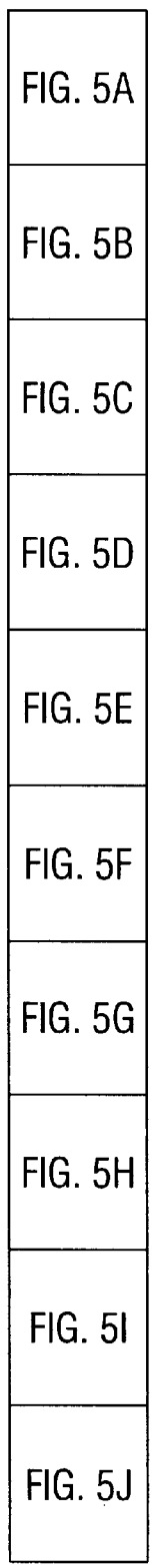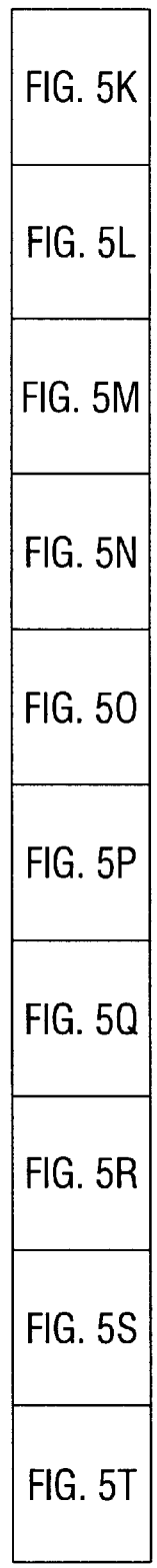
FIG. 5

```
GCTAAAGGTCTGGGACAGTGTACTTTGGGCTATCAGACGAGTACTCATG

CGGCCTACAGCTAAACAACTAGCTTCCTGACTCGGCCGGACCTAAGGAC

AAACGCTGACCGCGGCCGAAGGACTCAGATGACTGGAAACGGCCGACGC

AGGGCGGTCAGTCAGTCGTAGGTTCCAACTACCAACCGGCATTGTGCGC

CCACCTTGTGACCCGGTGCGTAGGCGTACGGCCGCACGTTACAGGCCGC

AAGCCTGCGCGGAAGCACGTCTAGCTTCTCCAGAAAGGCCCACTCCGTC

CCGCTGTAAAGATGTAGGTCCTAACTTAGTTCGGACCATATCCCCGCGG

TCAGGGCTCGCAGTAGCACCTACGGCAAGCTGCCGACTGCTGTCGCTCG

ATGGCTACCGGCCGCACTGAAGAAAGACGCGGAACGGCGACTGTATCTA
 K   G   I   A   P   T   V   E   K   Q   A   K   G   S   V   Y   I
```

FIG. 5B

```
 901 CGGCTACACTGGCGGCCCCTTCCGGTCGAGCCACATCAGGCCCGACG
      G  H  I  G  G  P  F  A  L  E  T  Y  D  P  S

1001 TCGCGCTTCTACAACTCGTGGCCCGTCCACTACAGGAAGTCCAGGTG
      L  A  F  I  N  L  V  P  C  T  I  D  K  L  D  V

1101 TCAGGAACTACTTGACTGCCTTCCAGAGCGGCCGGACTAGGCCCGAC
      F  D  K  I  F  Q  R  F  T  E  G  A  Q  D  P  S

1201 CTCGTCTAGTTGGTACAACTGCATGAAGACTGGGCAGTCCGACTTTC
      L  L  D  V  M  N  V  Y  K  Q  G  T  L  S  F

1301 CACAGCTGGCGGTCTAGCTACAGCTGCAAGACGTGGGTCCGGCTCTC
      T  D  V  A  L  D  I  D  V  N  Q  V  W  A  S  L

1401 CGTGGAACAGGCCCACGTCGCGGCGACATGTAGTCCGACTTCCGCGGC
      R  V  K  D  P  H  L  A  S  Y  M  L  S  F  A  G

1501 TATCAGGTGCGTCGCCAGCTACATCGGCAACTACATCAGCAGCTCGC
      Y  D  V  C  R  D  I  Y  G  N  I  Y  D  D  L
```

FIG. 5C

```
ACCAGTCAGGGAACTCGCGGGATCTCCGTAGGCCGCCGTGGTCCACTAGGACC
 S  T  L  G  K  L  A  R  S  A  D  P  P  V  L  H  D  Q

AAGGACAGGCGGGTCGTGGTGCGGCGGTAACTCCTTCGGCAACAAGACCATCT
  E  Q  G  G  L  V  V  G  G  N  L  F  G  N  N  Q  Y

AGCTTCTAGGTAAAGAGGTACGCGTCCTTCAAGAACTGGAACAGGCCCAGCAG
  P  F  I  W  K  E  M  R  L  F  N  K  V  K  D  P  D  D

CGAACTCGCTGTCCTTCCAGGTCAAGTCGTCGAGTGGCCCCTACAACGGGTAC
 P  K  L  S  L  F  T  W  N  L  L  E  G  P  I  N  G  M

GTCCAACAGGCCCCAGAACTTCAGCTGGCCGCACTGGTACCAGTGCTCCAACG
  L  N  D  P  T  K  F  D  V  P  T  V  M  T  V  L  N

GGGACTGTCTATGGCTCGTCTAACTGGAACAGCTGCGGCACCCGAAGCGCGTC
 G  Q  C  I  G  L  L  N  V  K  D  V  G  H  A  E  R  L

ACTCGCGCGCCAGCGGGACTAGGCCTATCGGGGTCAGCTAGTCCATCTGCAGG
 T  L  A  R  D  A  Q  D  P  Y  G  W  D  I  L  Y  V  D
```

FIG. 5D

```
1601 ACCGGCCACCGGTCGTCAGGGAACTACCACCTCGCCAGAAGGACCTA
      Q  G  T  A  L  L  G  K  I  T  S  R  D  E  Q  I

1701 CGACCCGAAGCCCGCGCGGGAGCCCAGCCAGTATCGCTATCTCCTGG
      P  Q  A  E  P  A  G  E  P  R  D  Y  R  Y  L  V

1801 GAGCCGCAACTCGTCTAAGAGGTACGGGACTGGGTCGAACGCCGACA
      E  A  N  L  L  N  E  M  G  Q  G  L  K  R  S

1901 TAGCGACAGGAGACTAAGACAGACCACTCGGACGACAAGCTAGTCGG
               S/D

2001 GGAACCGCCGGCCCCGCCCGCTGGACTCGCGTCACCGTCCGAACCAC
      A  K  A  A  P  A  P  S  R  L  A  T  A  P  K  T

2101 CACTGCGTCCCGGAACAAGAGCGCTGCCCAGAGGACCTCGGCCAGGA
      H  R  L  A  K  N  E  R  R  T  E  Q  L  R  D

2201 AGCTGGTCCTAGCTGTACGCGAAGAACTCGCGGTAGACTCGCAACTG
      D  V  L  I  S  M  R  K  K  L  A  M  Q  A  N  V
```

FIG. 5E

```
CAGCCAGTACATCCCGGCCAACTGGTCCCGCATCTGCTAGTCCTCGCCGTGCC
  D  T  M  Y  P  R  N  V  L  A  Y  V  I  L  L  P  V

TCGAACAGGAGCGACATCTGCCGGACGAACCCCGACTGCGGCCACAGCTACCG
  L  K  D  E  S  Y  V  A  Q  K  P  S  V  G  T  D  I  A

TCAGCTCGTAGAGGACCCACTCAAACAGGCCGGCCTACAGCTACCCCTTGTAC
Y  D  L  M  E  Q  T  L  K  D  P  R  I  D  I  P  F  M
                                              ←——— PhbC

CGAACTGCGAGTTAGCCGGCCTAACCAGAACCACCACGCGGCCGCACGGCCTC
        *  D  A  P  N  T  K  T  T  R  R  R  A  P

CGGCCGAGGAGTGGCCGGTCCCGACGCTGCGCTGCAAGGTCTAGCGCGTCCGA
  A  P  E  E  G  A  L  A  A  V  R  R  E  L  D  R  L  S

CCTCCCACGCGTCGAGCGACGCCCAGCCGTACAAGTTACGCGGGTCCAAGAGC
  Q  L  T  P  L  E  S  R  T  P  M  N  L  A  G  L  N  E

GTCGGCCGGCACCTACGCCCGCATAAGGCCACACCGCTGGAGCAGCCGTATCC
  L  R  G  H  I  R  A  Y  E  P  T  A  V  E  D  A  Y
```

FIG. 5F

```
2301 GCGGAAGCGTCGTCCGCTGGGTCAACAGCATCTCGCGCGCGCGGCTC
      A  G  E  C  C  A  V  W  N  D  Y  L  A  R  A  S

2401 CTGGCTGAAGTACGGCTCGAACCACATCTGCAACCACATAAGGACCT
      V  S  K  M  G  L  K  T  Y  V  N  T  Y  E  Q

2501 AGGAGCGCCCACATCGGCTCTGGCCCGCGGCTCTCCCGAGCTAGTTC
      E  E  R  T  Y  G  L  G  P  A  S  L  A  R  D  L

2601 CGCTGTAGCTCCTGTAGTACGCGACGGTCAACAGCTCGCCGTCGAGG
      P  S  M  S  S  M  M  R  Q  W  N  D  L  P  L  E

2701 CTTCGCGAAGACGTACAGAAGCTCGCAGAACCAGGTCTCGAGGTTCG
      F  R  K  Q  M  D  E  L  T  K  T  W  L  E  L
```

FIG. 5G

```
AGCTACCAAAACGGCGACAGCTACTGTGGGACCTACATCCTCGGGTACACGAG
 D  I  T  K  G  S  D  I  V  G  Q  I  Y  S  G  M  H  E

CGCGCCGGACTATGAGGTACCGCGACGCGTAGTCGAGGACTATGACCGAGACG
 L  A  A  Q  Y  E  M  A  S  R  M  L  E  Q  Y  Q  S  Q

TGACAGGAACTTGACGAGCACCCCGTACAACGCGTCGTACAGCGGGCCGTAGC
 S  D  K  F  Q  E  H  P  M  N  R  L  M  D  G  P  M

GTCTTGCTGTAGTCCGCGACGTACCACAACGGCGGCAGCAGCTCGCTCGGCGA
 W  F  S  M  L  R  Q  M  T  N  G  G  D  D  L  S  G  S

GCAACGGCCGCAACGGGAGCAGCCGCGCAAACCGCTTCCACAGCCGCTCTGCC
 G  N  G  A  N  G  E  D  A  R  K  A  F  T  D  A  L  R
```

FIG. 5H

```
2801 TTCTTCAAGAACGGGACGAGGTAGTAGAAAAGGTACTTGCTCGCACTGT
      F  F  N  K  G  Q  E  M  M  K  E  M  F  S  R  S

2901 GGGTCCCGCAGAACCGGCTTGACCTCCGCGACAGGTCTGGGTACCGGAA
      E  W  P  T  T  A  S  S  S  A  S  D  L  G  M  A  K

ATCGTCATTGAAGAAATTAGTGTTGCTCATGGACGTACCCTCCTCGTGG
3001 TAGCAGTAACTTCTTTAATCACAACGAGTACCTGCATGGGAGGAGCACC
      D  D  N  F  F  N  T  N  S  M        S/D
                ←—— ORF2

"-10"          •mRNA▸
     ATGCGTAGAATCCACAGGCCGCGACCCCATATCGGGGACGCTCGTCCAT
3101 TACGCTTCTTAGGTGTCCGGCGCTGGGGTATAGCCCCTGCGAGCAGGTA

V  D  A  G  R  S  A  I  G  T  F  G  G  S  L  S
3201 CGTCGACGCCGGCCGCAGTGCCATCGGAACCTTCGGCGGCAGTCTGTCG

R  T  G  L  A  P  E  Q  I  D  E  V  I  L  G  Q  V
3301 CGTACCGGACTCGCGCCGGAACAGATCGACGAGGTGATTCTCGGCCAGG

G  L  P  H  S  V  P  A  M  T  I  N  K  V  C  G
3401 CGGGGCTACCGCATTCGGTGCCGGCCATGACCATCAACAAGGTCTGCGG
```

FIG. 5I

```
CTAGGCCCCGCCCGCCCGCGGTACCGAAAGGTGGTGACTAGCTACCGGCGGA 5'
 L   D   P   A   A   P   A   M   A   K   W   W   Q   D   I   A   A

CGCCGAGTACAGCCAGGTCAACAGGGTCATGAACGCAACGTCAAGCTCGGT 5'
  R   S   M   D   T   W   N   D   Y   K   R   Q   L   E   L   W

"-35"
CGCGTGGTGTTGGGCGAACGGTATCATGTGGATTTGTGCACTGCAACAAAG 3'
GCGCACCACAACCCGCTTGCCATAGTACACCTAAACACGTGACGTTGTTTC 5'
           ←————                                      ────────
             MRNA              "-10"                    "-35"

phbA ——————→
                     S/D           M   S   E   N   I   V   I
TTCCAATCAGAATCCAGAGGACATCCACGCCATGAGCGAGAACATCGTCAT 3'
AAGGTTAGTCTTAGGTCTCCTGTAGGTGCGGTACTCGCTCTTGTAGCAGTA 5'

S   L   S   A   T   E   I   G   T   A   V   L   K   G   L   L   A
TCACTCTCGGCCACCGAGATCGGCACCGCCGTGCTCAAGGGGCTGCTGGCG 3'

L   T   A   G   V   G   Q   N   P   A   R   Q   T   T   L   H   A
TGCTGACCGCCGGCGTGGGCCAGAACCCCGCCCGTCAGACCACGCTGCACG 3'

S   G   L   K   A   V   H   L   A   M   Q   A   I   A   C   G   D
CAGCGGTCTGAAGGCGGTGCATCTGGCGATGCAGGCCATCGCCTGCGGGGA
```

FIG. 5J

```
             A  D  I  V  I  A  G  G  Q  E  S  M  S  Q  S  S  H
3501    TGCCGACATCGTCATCGCCGGCGGTCAGGAGAGCATGAGCCAGTCCTCGC

K  D  T  M  I  V  D  G  L  W  D  A  F  N  N  Y  H
3601    AAGGACACCATGATCGTCGACGGCCTCTGGGATGCCTTCAACAACTATCA

Q  Q  D  A  F  A  A  A  S  Q  Q  K  T  E  A  A
3701    AGCAGCAGGACGCCTTCGCCGCCGCCTCGCAGCAGAAGACCGAGGCCGCG

R  K  G  D  P  K  V  F  D  A  D  E  F  P  R  H  G
3801    GCGCAAGGGCGATCCGAAGGTGTTTGATGCCGACGAGTTCCCGCGTCACG

G  S  V  T  A  G  N  A  S  G  I  N  D  G  A  A  M
3901    GGCAGCGTCACGGCGGGTAACGCCTCCGGCATCAACGACGGGGCGGCCAT

A  R  L  V  A  F  A  S  A  G  V  D  P  A  I  M
4001    TGGCGCGTCTGGTGGCCTTCGCCAGCGCCGGTGTCGATCCGGCGATCATG

T  P  A  D  L  D  L  I  E  A  N  E  A  F  A  A  Q
4101    GACCCCGGCGGATCTGGATCTGATCGAGGCCAACGAAGCCTTCGCCGCGC
```

FIG. 5K

```
 V  L  P  R  S  R  D  G  Q  R  M  G  D  W  S  M
ACGTCCTGCCGCGTTCGCGCGACGGTCAGCGCATGGGCGACTGGTCGATG

M  G  T  T  A  E  N  I  A  Q  K  Y  G  F  T  R  E
CATGGGCACCACCGCCGAGAACATCGCCCAGAAGTACGGCTTTACGCGCG

Q  K  A  G  R  F  Q  D  E  I  I  P  I  E  I  P  Q
CAGAAGGCTGGCCGCTTCCAGGACGAGATCATTCCGATCGAGATTCCGCA

T  T  A  E  S  L  G  K  L  R  P  A  F  S  K  D
GCACCACGGCCGAGAGTCTGGGCAAGCTGCGTCCGGCCTTCTCGAAGGAC

V  V  V  M  K  E  S  K  A  K  E  L  G  L  K  P  M
GGTCGTGGTGATGAAGGAGTCCAAGGCCAAGGAACTGGGTCTGAAGCCGA

G  T  G  P  I  P  A  S  T  K  C  L  E  K  A  G  W
GGGACGGGCCCGATCCCGGCGTCGACCAAGTGCCTGGAGAAGGCCGGCTG

A  M  S  V  N  Q  D  M  G  W  D  L  S  K  V  N
AGGCCATGTCGGTCAACCAGGACATGGGCTGGGATCTGTCCAAGGTCAAC
```

FIG. 5L

```
              V  N  G  G  A  I  A  I  G  H  P  I  G  A  S  G
4201 GTCAACGGCGGCGCCATCGCCATCGGTCATCCGATCGGCGCCTCCGG

G  L  A  T  L  C  I  G  G  G  Q  G  V  A  L
4301 AGGGTCTGGCGACGCTGTGCATCGGCGGCGGCCAGGGCGTGGCGCTG

4401 AGCCTCCTGAATCGCTCCAGGCACTGAACGCCCTGCCGATCCCGGAT

ORF4——▶
     SmaI         M  N  S  E  R  I  I  K  K  Y  P  N
4501 CCCGGGTGCCCATGAACAGCGAGCGCATCATCAAGAAGTATCCGAAC

D  L  V  M  S  G  Q  P  F  R  V  L  D  S  A  N
4601 CGATCTGGTGATGAGCGGACAGCCCTTCCGCGTCCTCGACAGCGCCA

E  T  G  G  Q  P  L  F  S  A  N  M  L  A  Q  I
4701 ACCGGCGGTCAGCCGCTGTTCAGCGCCAACATGCTGGCCCAGATCAT
```

FIG. 5M

```
A   R   V   L   V   T   L   L   Y   E   M   Q   K   R   D   A   K   K
TGCGCGCGTGCTCGTGACCCTGCTCTATGAGATGCAGAAGCGCGACGCCAAGA

A   V   E   R   M   *
GCGGTCGAGCGGATGTGAGCCGTCGTCCGCCGGTCTGAATCGCCGGCGGACCG

CGGTGGGGCGTTTGCGCGCTTGGGGTAGACTTGCCGAACGACCAGCCGAACCG

R   R   L   Y   D   T   E   V   S   R   Y   I   T   L   A   D   V   R
CGCCGCCTCTACGACACCGAGGTCAGCCGCTATATCACCCTCGCCGATGTGCG

D   S   D   I   T   R   S   I   L   L   Q   I   M   L   E   E   E
ATGACAGCGATATCACCCGTTCCATCCTGCTCCAGATCATGCTGGAGGAGGAG

I   R   F   Y   G   G   T   L   Q   G   T   F   A   R   Y   L   E   S
CCGCTTCTACGGCGGCACCCTTCAGGGCACCTTCGCCCGCTATCTGGAATCTT
```

FIG. 5N

```
          S   L   D   L   F   A   K   Q   Q   Q   E   V   T   K   A
4801 CACTCGACCTGTTCGCCAAGCAGCAACAGGAAGTGACCAAGGCACTC

I   W   A   D   L   Q   D   E   L   M   R   A   A   G   F   P
4901 CTGGGCTGATCTCCAGGACGAACTCATGCGCGCGGCTGGCTTTCCGG

"-10"(?)
5001 GCCGTCGGTCACAGCTTTATTGTGCAATGCAACATTGCTGCACTGCA

E   W   T   N   K   S   V   E   R   M   T   S   F   G   E
5101 ACGAGTGGACCAACAAGAGCGTCGAGCGCATGACCAGCTTCGGTGAG

L   Y   M   D   H   S   M   R   L   M   K   L   A   T   E   S
5201 CCTGTACATGGATCACAGCATGCGCCTGATGAAGCTGGCCACCGAGT

S   E   R   V   M   A   E   S   K   A   T   M   Q   F   F   G
5301 AGCGAGCGCGTCATGGCCGAGAGCAAGGCCACCATGCAGTTCTTCGG

E   D   L   R   K   S   V   A   V   *
5401 GCGAAGATCTGCGCAAGAGCGTCGCCGTCTAAAGACGCCGACCTCTG
```

FIG. 50

```
 L   T   D   N   P   F   G   T   V   T   R   L   T   Q   K   N   V   E
ACCGACAATCCCTTCGGGACGGTGACACGCCTGACTCAGAAGAACGTCGAGAT

V   A   P   R   K   K   E   *                           "-35"(?)
TCGCGCCGCGCAAGAAAAAGAATAATGAGGATTGCGAAAATTGCGCTTGACG

ORF5 ──────▶
       S/D              M   N   T   T   D   S   L   K   T   V   N
CAAACCTTAC GGAG AGATGATCATGAACACCACCGACAGCCTCAAGACCGTCA

L   N   V   R   L   F   E   K   L   A   A   R   Q   M   D   A   V   N
CTGAACGTGCGTCTGTTCGAGAAGCTGGCCGCCCGTCAGATGGACGCCGTGAA

K   G   Y   N   D   L   F   K   G   Q   V   D   A   T   K   E   L
CCAAGGGTTACAATGACCTCTTCAAGGGTCAGGTCGACGCCACCAAGGAACTG

D   A   R   D   E   Y   R   V   W   F   E   K   S   L   N   D   V   S
CGATGCCCGCGACGAATACCGCGTGTGGTTCGAGAAGAGCCTGAACGACGTCA

──────▶        ◀──────            ──────▶       ◀──
GGCCATCGCGATCCAGGGATGGATCGCCATTGGTCATGCTTCCGGATCGGCCG
```

FIG. 5P

```
                                                                  phbB ──▶
                    S/D              M  A  R  I  A  L  V  T  G  G
5501 GGAGCACGCCCAATGGAACCAACGCTTCACCTTGCCTGCCGCTTGGTA
5601 AAGATTCCTGGAGGAACCCCATGGCTCGTATCGCACTCGTCACCGGCG T  V  V  A  N  C  H  P  S  E  A  A  A  A  E  E
5701 CACCGTCGTGGCGAACTGCCATCCGTCCGAGGCGGCCGCCGCCGAAGA D  V  S  S  F  D  D  S  A  R  M  V  R  E  I  T
5801 GACGTGTCCTCGTTCGACGACAGCGCGCGCATGGTTCGCGAGATCACA K  T  F  K  K  M  E  Q  A  H  W  E  A  V  I  N
5901 ACAAGACCTTCAAGAAGATGGAGCAGGCGCACTGGGAGGCCGTGATCA L  E  R  G  F  G  R  I  I  N  I  S  S  V  N  G
6001 GCTGGAGCGCGGCTTCGGGCGTATCATCAACATCTCGTCGGTCAACGG H  G  F  T  M  A  L  A  Q  E  G  A  S  K  G  V
6101 CACGGCTTCACCATGGCTCTGGCTCAGGAGGGTGCGTCCAAGGGCGTG
```

FIG. 5Q

```
GTAAAGTGGCCTTGAAGTTCGACGACACTGTTCATCGTTCTCAATAGTTCCA

I  G  G  I  G  T  S  I  C  T  R  L  A  K  D  G  C
GCATCGGCGGCATCGGCACTTCGATCTGCACACGCCTGGCAAAGGATGGCTG

W  K  Q  A  R  A  A  E  G  F  D  I  A  V  F  T  A
GTGGAAGCAGGCCCGTGCCGCCGAGGGGTTCGACATCGCCGTCTTCACCGCT

E  Q  V  G  P  I  D  I  L  V  N  C  A  G  I  T  R  D
GAGCAGGTCGGTCCCATCGACATCCTGGTCAACTGTGCCGGCATCACCCGCG

V  N  L  N  S  V  F  N  V  T  R  Q  V  W  D  G  M
ACGTCAACCTCAACAGCGTCTTCAACGTCACCCGTCAGGTGTGGGACGGGAT

Q  R  G  Q  F  G  Q  A  N  Y  S  A  A  K  A  G  M
TCAGCGCGGCCAGTTCGGTCAGGCCAACTATTCCGCCGCCAAGGCCGGTATG

T  V  N  T  I  S  P  G  Y  V  E  T  A  M  T  L  A  M
ACCGTCAACACCATCTCGCCCGGCTATGTCGAGACGGCCATGACCCTGGCGA
```

FIG. 5R

```
          N  D  D  V  R  N  S  I  I  S  G  I  P  M  R
6201 TGAACGACGATGTGCGCAACAGCATCATCAGCGGTATTCCGATGCG

E  S  G  Y  M  T  G  A  N  L  P  V  N  G  G
6301 CGAGAGCGGTTATATGACGGGCGCCAATCTGCCGGTCAACGGCGGT

6401 GCCCGGTGTTTCAGGATCTCACCGAGTCCTCCTCGTCTCTCTCATC

ORF7─────▶
                    M  N  A  V  M  T  D  V  R  D  L  I
6501 CGCCCATCCGATGAACGCTGTGATGACCGACGTACGCGATCTGATC

G  L  Q  V  E  G  E  R  P  L  Q  R  L  V  S  G
6601 GGTTTGCAAGTGGAGGGCGAACGGCCGCTCCAGCGGCTGGTGTCGG

I  L  V  H  H  G  W  F  W  K  N  E  N  P  C
6701 CCATTCTGGTCCATCATGGCTGGTTCTGGAAGAACGAGAATCCCTG

L  I  A  Y  H  L  P  L  D  A  H  P  E  L  G
6801 TCTGATCGCCTATCATCTGCCGCTCGATGCCCATCCCGAACTCGGC

L  A  N  G  L  L  W  A  A  I  G  S  A  H  D  A
6901 CTGGCCAATGGTCTGCTGTGGGCGGCGATTGGCTCAGCCCATGACG
```

FIG. 5S

```
  R   M   A   Q   P   N   E   I   A   A   A   I   A   F   L   A   G   D
TCGCATGGCTCAGCCTAATGAGATCGCCGCCGCCATCGCTTTCCTGGCCGGCGA

L   F   M   H   *
CTGTTCATGCATTGATTTAGATCATACCGGGCCGAATACAAAACACTGACAATG

ATGAGACGTTTACAGCCCGGCGCCAGCCGGGCTTTTTTTTGTGTAGAATCGAAT

R   Y   C   D   D   V   L   D   A   A   R   F   A   D   Y   A   P   N
CGCTACTGCGATGACGTGCTCGACGCGGCGCGCTTCGCCGACTATGCGCCGAAT

V   T   A   S   A   A   L   I   E   A   A   I   A   E   H   A   D   A
GCGTGACGGCCAGCGCCGCGTTGATCGAGGCCGCGATCGCGGAGCACGCCGACG

L   I   G   I   K   G   Q   R   A   R   T   L   L   S   A   G   V   S
CCTGATCGGCATCAAGGGGCAGCGCGCAAGGACATTGCTCAGCGCGGGTGTGAG

N   N   A   T   L   G   R   R   L   D   F   I   D   M   E   P   T   A
AACAATGCCACACTCGGTCGCCGGCTCGATTTCATCGACATGGAACCGACCGCA

C   V   L   H   G   A   C   L   A
CCTGCGTCCTTCACGGAGCATGTCTCGCATC
```

```
C.v.    1  MSENIVIVDAGRSAIG-TFGGSLSSLSATEIGTA
A.e.    1           MTDVVISAARTAVG-KFGGSLAKIPAPELGAV
Z.r.    1         MSTPSIVIASARTAVG-SFNGAFANTPAHELGAT
E.c.    1        MEQVVIVDAIRTPMGRSKGGAFRNVRAEDLSAH
S.u.    1       MSQNVYIVSTARTPIG-SFQGSLSSKTAVELGAA
R.n.    1        MALLRGVFIVAAKRTPFG-AYGGLLKDFTATDLTEF

C.v.   34  VLKGLLAR-TGL--APEQIDEVILGQV-LTAGVGQN
A.e.   33  VIKAALER-AGV--KPEQVSEVIMGQV-LTAGSGQN
Z.r.   34  VISAVLER-AGV--AAGEVNEVILGQV-LPAGEGQN
E.c.   34  LMRSLLARNPAL--EAAALDDIYWGCVQQTILEQGEN
S.u.   34  ALKGALAK-VPELDASKDFDEIIFGNV-LSANLGQA
R.n.   35  AARAALSA-GKV--PPETIDSVIVGNV-MQSSSDAA

C.v.   66  -PARQTTLHAGLPHSVPAMTINKVCGSGLKAVHLAM
A.e.   65  -PARQAAIKAGLPAMVPAMTINKVCGSGLKAVMLAA
Z.r.   66  -PARQAAMKAGVPQEATAWGMNQLCGSGLRAVALGM
E.c.   68  -IARNAALLAEVPHSVPAVTTVNRLCGSSMQALHDAA
S.u.   68  -PARQVALTAGLGNHIVATTVNKVCASAMKAIILGA
R.n.   68  YLARHVGLRVGVPTETGALTLNRLCGSSFQSIVSGC

C.v.  101  QAIACGDADIVIAGGQESMSQSSHVLPRSRDGQRMG
A.e.  100  NAIMAGDAEIIVIAGGQENMSAAPHVLPGSRDGFRMG
Z.r.  101  QQIATGDASIITVAGGMESMSMAPHCAHLA--GVKMG
E.c.  103  RMIMTGDAQACLVGGVEHMGH-----VPMSHGVDFHP
S.u.  103  QSIKCGNADVVAGGCESMINAPYYMBAARGGAKFG
R.n.  104  QEICSKDAEVVLCGGTESMSQSPYSVRNVRFGTKFG
```

FIG. 6A

| | | | |
|---|---|---|---|
| C.v. | 137 | -DWSMKDTMIVDGLWDAFNNYHMGTTAENIAQKYGF |
| A.e. | 136 | -DAKLVDTMIVDGLWDVYNQYHMGITAENVAKEYGI |
| Z.r. | 136 | -DFKMIDTMIKDGLTDAFYGYHMGTTAENVAKQWQL |
| E.c. | 135 | -GLS-RNVAKAAGM-----MGLTAEMLARMHGI |
| S.u. | 139 | -QTVLIDGVERDGLNDAYDGLAMGVHAEKCARDWDI |
| R.n. | 140 | LDLKLEDTLW-AGLDTQHVKLPMGMTAENLAAQYNI |

| | | |
|---|---|---|
| C.v. | 172 | TREQQDAFAAASQQKTEAAQKAGRFQDEIIPIEIPQ |
| A.e. | 171 | TREAQDEFAAAQDEFAVGSQNKAEAAQKAGKFDEEIVPLIPQ |
| Z.r. | 171 | SRDEQDAFAVASQNKAEAAKKDGRFKDEIVPFIVKG |
| E.c. | 161 | SREMQDAFAARSHARAWAAATQSAAFKNEIIPTGGHD |
| S.u. | 174 | TRDQQDSFAIESYQKSQQSQKEGKFDNEIVPVTIKG |
| R.n. | 175 | SREDCDRYALQSQQRWKAANEAGYFNEEMAPIEVKT |

| | | |
|---|---|---|
| C.v. | 208 | RKGDPKVFDADEFPRHGTTAESLGKLRPAF-SKD-G |
| A.e. | 207 | RKGDPVAFKTDEFVRQGAILDSMSGLKPAF-DKA-G |
| Z.r. | 207 | RKGDITV-DADEYIRHGAILDSMAKLRPAF-DKE-G |
| E.c. | 197 | ADGVLKQFNYDEVIRPETTIVEALATLRPAFDPVN-G |
| S.u. | 210 | FRGKPDTQVTNDEEPARLHVEKLKSARTVF-QRENG |
| R.n. | 211 | KKGKQTM-QVDEHARPQTTLEQLQNLPPVF-KKE-G |

FIG. 6B

```
C.v. 242 SVTAGNASGINDGAAMVVVMKESKAKELGLKPMARL
A.e. 241 TVTAGNASGLNDGAAAVVVMSAAKAKELGLTPLATI
Z.r. 240 TVTAGNASGLNDGAAAALMSEAEASRRGIQPLGRI
E.c. 232 MVTAGTSSALSDGAAAMLVMSESRAHELGLKPRARV
S.u. 245 TVTAANASPINDGAAAILVSERVLKEKNLKPLAIV
R.n. 244 TVTAGNASGMSDGAGVVIIASEDAVKKHNFTPLARV

C.v. 278 VAFASAGVDPAIMGTGPIPASTKCLEKAGWTPAD-L
A.e. 277 KSYANAGVDPKVMGMGPVPASKRALSRAEWTPQD-L
Z.r. 276 VSWATVGVDPKVMGTGPIPASRKALERAGWKIGD-L
E.c. 268 RSMAVVGCDPSIMGYGPVPASKLALKKAGLSASD-I
S.u. 281 KGWGEAAHLPADFTWAPSLAVPKALKHAGIEDINSV
R.n. 280 VGYFVSGCDPAIMGIGPVPAITGALKAGLSLKD-M

C.v. 313 DLIEANEAFAAQAMSVNQDMGWDL---SKVNVNGGA
A.e. 312 DLMEINEAFAAQALAVHQQMGWDT---SKVNVNGGA
Z.r. 311 DLVEANEAFAAQACAVNKDLGWDP---SIVNVNGGA
E.c. 303 GVFEMNEAFAAQILPCIKDLGLIEQIDEKINLNGGA
S.u. 317 DYFEFNEAFSVVGLVNTKILKLDP---SKVNVYGGA
R.n. 315 DLIDVNEAFAPQFLAVQKSLDLDP---SKTNVSGGA
```

FIG. 6C

```
C.v.  346  IAIGHPIGASGARVLVTLLYEMQKRDAKKGLATLCI
A.e.  345  IAIGHPIGASGCRILVTLLHEMKRRDAKKGLASLCI
Z.r.  344  IAIGHPIGASGARILNTLLFEMKRRGARKGLATLCI
E.c.  339  IALGHPLGCSGARISTILNLMERKDVQFGLADGCV
S.u.  350  VALGHPLGCSGARVVTLLSILQEGGKIGVAAICN
R.n.  348  IALGHPLGGSGSRITAHLVHELRRRGGKYAVGSACI

C.v.  382  GG-GQGVALAVERM
A.e.  381  GG-GMGVALAVERK
Z.r.  380  GG-GMGVAMCIESL
E.c.  375  SGLGQGIATVFERV
S.u.  387  GG-GGASSVVIEKL
R.n.  384  GG-GQGISLIIQNTA
```

Homology to ketothiolase of C.vinosum:

68.2%
59.4%
43.0%
42.7%
42.6%

Comparison of amino sequences of the -ketothiolases encoded by Chromatium vinosum (C.v.), Alcaligenes eutrophus (A.e.), Zoogloea ramigera (Z.r.), Escherichia coli (E.c.), Saccharomyces uvarum (S.u.) and Rattus norvegicus (R.n.).

FIG. 6D

```
C.v.   1                   MARIALVTGGIGTSICTRLAKDGCTVVANCHP
A.e.   1                   MTQRIAYVTGGMGGIGTAICQRLAKDGFRVVAGCGP
Z.r.   1   MSRVALVTGGSRGIGAAISIALKAAGYKVAASYAG

C.v.  36  SEAAAAEEWKQARAAEGFDIAVFTA------DVSSF
A.e.  37  -NSPRREKWLEQQKALGFDFIASEG------NMADW
Z.r.  36  -ND-----DAAKP-----FKAETGIAVYKWDVSSY

C.v.  66  DDSARMVREITEQVGPIDILVNCAGITRRKTFKKME
A.e.  66  DSTKTAFDKVKSEVGEVDVLINNAGITRDVVFRKMT
Z.r.  60  EACVEGIAKVEADLGPIDVLVNNAGITKDAMFHKMT

C.v. 102  QAHWEAVINVNLNSVFNVTRQYWDGMLERGFGRIIN
A.e. 102  RADWDAVIDTNLTSLFNVTKQVIDGMADRGWGRIVN
Z.r.  96  PDQWNAVINTNLTGLFNMTHPVWSGMRDRSFGRIVN
```

FIG. 7A

| FIG. 7A |
|---------|
| FIG. 7B |

FIG. 7

```
C.v. 138 ISSVNGQRGQFGQANYSAAKAGMHGFTMALAQEGAS
A.e. 138 ISSVNGQKGQFGQTNYSAKAGLHGFTMALAQEVAT
Z.r. 132 ISSINGQKGQMGQANYSAAKAGDLGFTKALAQEGAA

C.v. 174 KGVTVNTISPGYVETAMTLAMNDDVR-NSIISGIPM
A.e. 174 KGVTVNTVSPGYIATDMVKAIRQDVL-DKIVATIPV
Z.r. 168 KGITVNAICPGYIGTEMVRAIPEKVLNERIIPQIPV

C.v. 209 RRMAQPNEIAAAIAFLAGDESGYMTGANLPVNGGLF
A.e. 209 KRLGLPEEIASICAWLSSEESGFSTGADFSLNGGLH
Z.r. 204 GLRGEPDEIARIVVFLASDEAGFITGSTISANGGQF

C.v. 245 MHHomology to reductase of C. vinosum:
A.e. 245 MG 56.4%
Z.r. 240 FV 48.3%
```

Comparison of amino acid sequences of reductases encoded by C. vinosum (C.v.), A. eutrophus (A.e.) and Z. ramigera (Z.r.).

FIG. 7B

| Strain (plasmid) | relevant markers | Medium |
|---|---|---|
| S17-1(pHP1014) | none | LB-Tc-Glu |
| S17-1 (pHP1014::PP10) | phbA$^+$, phbB$^+$, phbC$^+$, ORF2$^+$ | LB-Tc-Glu |
| S17-1 (pHP1014::EP94) | phbA$^+$, phbB$^+$, phbC$^-$, ORF2$^+$ | LB-Tc-Glu |
| S17-1 (pSUP202) | none | LB-Tc-Glu |
| S17-1 (pSUP202::PP10) | phbA$^+$, phbB$^+$, phbC$^+$, ORF2$^+$ | LB-Tc-Glu |
| XL1-Blue (KS) | none | LB-Ap-Glu |
| XL1-Blue (KS) | none | LB-Ap-IPTG |
| XL1-Blue (KS::SE45+) | phbA$^+$, phbB$^-$, phbC$^+$, ORF2$^+$ | Lb-Ap-Glu |
| XL1-Blue (KS::SE45+) | phbA$^+$, phbB$^-$, phbC$^+$, ORF2$^+$ | LB-Ap-IPTG |
| XL1-Blue (KS::SE45-) | phbA$^+$, phbB$^-$, phbC$^+$, ORF2$^+$ | LB-Ap-Glu |
| XL1-Blue (KS::SE45-) | phbA$^+$, phbB$^-$, phbC$^+$, ORF2$^+$ | LB-Ap-IPTG |

FIG. 8A

SFIG. 8 (2/2)

| PHB synthase | Specific activity (U/g of protein) | | | Accumulation of PHB (% of cellular dry weight) |
|---|---|---|---|---|
| | -Ketothiolase | Acetoacetyl-CoA reductase | | |
| | | NADH-dependent | NADPH-dependent | |
| <0.1 | <20 | <20 | <20 | <0.1 |
| 6.1 | 1190 | 420 | 60 | 10.2 |
| 5.2 | 940 | 310 | 60 | 9.7 |
| <0.1 | <20 | <20 | <20 | <0.1 |
| 6.1 | 1320 | 320 | 60 | 12.1 |
| <0.1 | <20 | <20 | <20 | <0.1 |
| <0.1 | <20 | <20 | <20 | <0.1 |
| 6.0 | 1120 | <20 | <20 | <0.1 |
| 4.3 | 980 | <20 | <20 | <0.1 |
| 4.8 | 470 | <20 | <20 | <0.1 |
| 2.9 | 70 | <20 | <20 | <0.1 |
| <0.1 | 80 | 30 | <20 | <0.1 |
| <0.1 | 1870 | 610 | 40 | <0.1 |

FIG. 8B

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 4506 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Chromatium vinosum (xi) SEQUENCE DESCRIPTION: SEQ ID NO:1:

```
GCTTAAGTAG GTCCCGGTGA TAGAGGTTGA CGGCTCAAGC CTGAACTTGA AGCTAAAGGT      60

CTGGGACAGT GTACTTTGGG CTATCAGACG AGTACTCATG CCGCGAAGTG TGCCCTGCCG     120
```

-continued

```
ACTAGGACTG AGGTAGGCTA GGCGTAGAGC GCGGCCTACA GCTAAACAAC TAGCTTCCTG    180
ACTCGGCCGG ACCTAAGGAC TCACGAGGTA ACTAGGACCT CTTAGGTGTC GGCCCCCGCC    240
CGCTGGCTCG GAAACGCTGA CCGCGGCCGA AGGACTCAGA TGACTGGAAA CGGCCGACGC    300
GGCAGGCCTA AGCGCTACTG CAGTCTCGCC CCGCAAAGAG CGTATAAGCG TAGGGCGGTC    360
AGTCAGTCGT AGGTTCCAAC TACCAACCGG CATTGTGCGC GGGTGGGGCT ACACAGCCCA    420
CAGCGCGCGG GGACAGCCCG ACCGCGCGCG ACCACCTTGT GACCCGGTGC GTAGGCGTAC    480
GGCCGCACGT TACAGGCCGG ACGCCGCTCT GTGCAGGCGG GACCGAGACC CTGACCTTTG    540
TCGTTCCTCC TAAGCCTGCG CGGAAGCACG TCTAGCTTCT CCAGAAAGGC CCACTCCGTC    600
ACGGCTGCGG CTACAAGAAG CTCGTCGAGT AAGCCCAGTC ACCCTAGCCG ACCGCTGTAA    660
AGATGTAGGT CCTAACTTAG TTCGGACCAT ATCCCCGCGC AATTGCACTT CCGGTCGAGG    720
TTCAGGCGAG CTACTCGCTG CTGCGGGCCA CTCAGGGCTC GCAGTAGCAC CTACGGCAAG    780
CTGCCGACTG CTGTCGCTCG GCGGCCTTAA CGAGGCCGCC GAGCCCTTCG CAATAGCGAG    840
CAACTCGGTG AATGGCTACC GGCCGCACTG AAGAAAGACG CGGAACGGCG ACTGTATCTA    900
CGGCTACACT GGCGGCCCCT TCCGGTCGAG CCACATCAGG CCCGACGACC AGTCAGGGAA    960
CTCGCGGGAT CTCCGTAGGC CGCCGTGGTC CACTAGGACC TCGCGCTTCT ACAACTCGTG   1020
GCCCGTCCAC TACAGGAAGT CCAGGTGAAG GACAGGCGGG TCGTGGTGCG GCGGTAACTC   1080
CTTCGGCAAC AAGACCATCT TCAGGAACTA CTTGACTGCC TTCCAGAGCG GCCGGACTAG   1140
GCCCGACAGC TTCTAGGTAA AGAGGTACGC GTCCTTCAAG AACTGGAACA GGCCCAGCAG   1200
CTCGTCTAGT TGGTACAACT GCATGAAGAC TGGGCAGTCC GACTTTCCGA ACTCGCTGTC   1260
CTTCCAGGTC AAGTCGTCGA GTGGCCCCTA CAACGGGTAC CACAGCTGGC GGTCTAGCTA   1320
CAGCTGCAAG ACGTGGGTCC GGCTCTCGTC CAACAGGCCC CAGAACTTCA GCTGGCCGCA   1380
CTGGTACCAG TGCTCCAACG CGTGGAACAG GCCCACGTCG CGCGACATGT AGTCCGACTT   1440
CCGCGGCGGG ACTGTCTATG GCTCGTCTAA CTGGAACAGC TGCGGCACCC GAAGCGCGTC   1500
TATCAGGTGC GTCGCCAGCT ACATCGGCAA CTACATCAGC AGCTCGCACT CGCGCGCCAG   1560
CGGGACTAGG CCTATCGGGG TCAGCTAGTC CATCTGCAGG ACCGGCCACC GGTCGTCAGG   1620
GAACTACCAC CTCGCCAGAA GGACCTACAG CCAGTACATC CCGGCCAACT GGTCCCGCAT   1680
CTGCTAGTCC TCGCCGTGCC CGACCCGAAG CCCGCGCGGG AGCCCAGCCA GTATCGCTAT   1740
CTCCTGGTCG AACAGGAGCG ACATCTGCCG GACGAACCCC GACTGCGGCC ACAGCTACCG   1800
GAGCCGCAAC TCGTCTAAGA GGTACGGGAC TGGGTCGAAC GCCGACATCA GCTCGTAGAG   1860
GACCCACTCA AACAGGCCGG CCTACAGCTA CCCCTTGTAC TAGCGACAGG AGACTAAGAC   1920
AGACCACTCG GACGACAAGC TAGTCGGCGA ACTGCGAGTT AGCCGGCCTA ACCAGAACCA   1980
CCACGCGGCC GCACGGCCTC GGAACCGCCG GCCCCGCCCG CTGGACTCGC GTCACCGTCC   2040
GAACCACCGG CCGAGGAGTG GCCGGTCCCG ACGCTGCGCT GCAAGGTCTA GCGCGTCCGA   2100
CACTGCGTCC CGGAACAAGA GCGCTGCCCA GAGGACCTCG GCCAGGACCT CCCACGCGTC   2160
GAGCGACGCC CAGCCGTACA AGTTACGCGG GTCCAAGAGC AGCTGGTCCT AGCTGTACGC   2220
GAAGAACTCG CGGTAGACTC GCAACTGGTC GGCCGGCACC TACGCCCGCA TAAGGCCACA   2280
CCGCTGGAGC AGCCGTATCC GCGGAAGCGT CGTCCGCTGG GTCAACAGCA TCTCGCGCGC   2340
GCGGCTCAGC TACCAAAACG GCGACAGCTA CTGTGGGACC TACATCCTCG GGTACACGAG   2400
CTGGCTGAAG TACGGCTCGA ACCACATCTG CAACCACATA AGGACCTCGC GCCGGACTAT   2460
```

-continued

```
GAGGTACCGC GACGCGTAGT CGAGGACTAT GACCGAGACG AGGAGCGCCC ACATCGGCTC    2520

TGGCCCGCGG CTCTCCCGAG CTAGTTCTGA CAGGAACTTG ACGAGCACCC CGTACAACGC    2580

GTCGTACAGC GGGCCGTAGC CGCTGTAGCT CCTGTAGTAC GCGACGGTCA ACAGCTCGCC    2640

GTCGAGGGTC TTGCTGTAGT CCGCGACGTA CCACAACGGC GGCAGCAGCT CGCTCGGCGA    2700

CTTCGCGAAG ACGTACAGAA GCTCGCAGAA CCAGGTCTCG AGGTTCGGCA ACGGCCGCAA    2760

CGGGAGCAGC CGCGCAAACC GCTTCCACAG CCGCTCTGCC TTCTTCAAGA ACGGGACGAG    2820

GTAGTAGAAA AGGTACTTGC TCGCACTGTC TAGGCCCCGC CGCCCGCGGT ACCGAAAGGT    2880

GGTGACTAGC TACCGGCGGA GGGTCCCGCA CAACCGGCTT GACCTCCGCG ACAGGTCTGG    2940

GTACCGGAAC GCCGAGTACA GCCAGGTCAA CAGGGTCATG AACGCAACGT CAAGCTCGGT    3000

TAGCAGTAAC TTCTTTAATC ACAACGAGTA CCTGCATGGG AGGAGCACCG CGCACCACAA    3060

CCCGCTTGCC ATAGTACACC TAAACACGTG ACGTTGTTTC TACGCATCTT AGGTGTCCGG    3120

CGCTGGGGTA TAGCCCCTGC GAGCAGGTAA AGGTTAGTCT TAGGTCTCCT GTAGGTGCGG    3180

TACTCGCTCT TGTAGCAGTA GCAGCTGCGG CCGGCGTCAC GGTAGCCTTG GAAGCCGCCG    3240

TCAGACAGCA GTGAGAGCCG GTGGCTCTAG CCGTGGCGGC ACGAGTTCCC CGACGACCGC    3300

GCATGGCCTG AGCGCGGCCT TGTCTAGCTG CTCCACTAAG AGCCGGTCCA CGACTGGCGG    3360

CCGCACCCGG TCTTGGGGCG GGCAGTCTGG TGCGACGTGC GCCCCGATGG CGTAAGCCAC    3420

GGCCGGTACT GGTAGTTGTT CCAGACGCCG TCGCCAGACT TCCGCACGT AGACCGCTAC     3480

GTCCGGTAGC GGACGCCCCT ACGGCTGTAG CAGTAGCGGC CGCCAGTCCT CTCGTACTCG    3540

GTCAGGAGCG TGCAGGACGG CGCAAGCGCG CTGCCAGTCG CGTACCCGCT GACCAGCTAC    3600

TTCCTGTGGT ACTAGCAGCT GCCGGAGACC CTACGGAAGT TGTTGATAGT GTACCCGTGG    3660

TGGCGGCTCT TGTAGCGGGT CTTCATGCCG AAATGCGCGC TCGTCGTCCT GCGGAAGCGG    3720

CGGCGGAGCG TCGTCTTCTG GCTCCGGCGC GTCTTCCGAC CGGCGAAGGT CCTGCTCTAG    3780

TAAGGCTAGC TCTAAGGCGT CGCGTTCCCG CTAGGCTTCC ACAAACTACG GCTGCTCAAG    3840

GGCGCAGTGC CGTGGTGCCG GCTCTCAGAC CCGTTCGACG CAGGCCGGAA GAGCTTCCTG    3900

CCGTCGCAGT GCCGCCCATT GCGGAGGCCG TAGTTGCTGC CCCGCCGGTA CCAGCACCAC    3960

TACTTCCTCA GGTTCCGGTT CCTTGACCCA GACTTCGGCT ACCGCGCAGA CCACCGGAAG    4020

CGGTCGCGGC CACAGCTAGG CCGCTAGTAC CCCTGCCCGG GCTAGGGCCG CAGCTGGTTC    4080

ACGGACCTCT TCCGGCCGAC CTGGGCCGC CTAGACCTAG ACTAGCTCCG GTTGCTTCGG     4140

AAGCGGCGCG TCCGGTACAG CCAGTTGGTC CTGTACCCGA CCCTAGACAG GTTCCAGTTG    4200

CAGTTGCCGC CGCGGTAGCG GTAGCCAGTA GGCTAGCCGC GGAGGCCACG CGCGCACGAG    4260

CACTGGGACG AGATACTCTA CGTCTTCGCG CTGCGGTTCT TCCCAGACCG CTGCGACACG    4320

TAGCCGCCGC CGGTCCCGCA CCGCGACCGC CAGCTCGCCT ACACTCGGCA GCAGGCGGCC    4380

AGACTTAGCG GCCGCCTGGC TCGGAGGACT TAGCGAGGTC CGTGACTTGC GGGACGGCTA    4440

GGGCCTAGCC ACCCCGCAAA CGCGCGAACC CCATCTGAAC GGCTTGCTGG TCGGCTTGGC    4500

GGGCCC                                                              4506
```

(2) INFORMATION FOR SEQ ID NO:2:

(i) SEQUENCE CHARACTERISTICS:
        (A) LENGTH: 394 amino acids
        (B) TYPE: amino acid
        (D) TOPOLOGY: linear (ii) MOLECULE TYPE: protein (vi) ORIGINAL SOURCE:
    (A) ORGANISM: Chromatium vinosum (xi) SEQUENCE DESCRIPTION: SEQ ID NO:2:

```
Met Ser Glu Asn Ile Val Ile Val Asp Ala Gly Arg Ser Ala Ile Gly
 1               5                  10                  15

Thr Phe Gly Gly Ser Leu Ser Ser Leu Ser Ala Thr Glu Ile Gly Thr
             20                  25                  30

Ala Val Leu Lys Gly Leu Leu Ala Arg Thr Gly Leu Ala Pro Glu Gln
             35                  40                  45

Ile Asp Glu Val Ile Leu Gly Gln Val Leu Thr Ala Gly Val Gly Gln
 50                  55                  60

Asn Pro Ala Arg Gln Thr Thr Leu His Ala Gly Leu Pro His Ser Val
 65                  70                  75                  80

Pro Ala Met Thr Ile Asn Lys Val Cys Gly Ser Gly Leu Lys Ala Val
             85                  90                  95

His Leu Ala Met Gln Ala Ile Ala Cys Gly Asp Ala Asp Ile Val Ile
             100                 105                 110

Ala Gly Gly Gln Glu Ser Met Ser Gln Ser Ser His Val Leu Pro Arg
             115                 120                 125

Ser Arg Asp Gly Gln Arg Met Gly Asp Trp Ser Met Lys Asp Thr Met
 130                 135                 140

Ile Val Asp Gly Leu Trp Asp Ala Phe Asn Asn Tyr His Met Gly Thr
145                 150                 155                 160

Thr Ala Glu Asn Ile Ala Gln Lys Tyr Gly Phe Thr Arg Glu Gln Gln
             165                 170                 175

Asp Ala Phe Ala Ala Ser Gln Gln Lys Thr Glu Ala Ala Gln Asp
             180                 185                 190

Ala Gly Arg Phe Gln Asp Glu Ile Ile Pro Ile Glu Ile Pro Gln Arg
             195                 200                 205

Lys Gly Asp Pro Lys Val Phe Asp Ala Asp Glu Phe Pro Arg His Gly
 210                 215                 220

Thr Thr Ala Glu Ser Leu Gly Lys Leu Arg Pro Ala Phe Ser Lys Asp
225                 230                 235                 240

Gly Ser Val Thr Ala Gly Asn Ala Ser Gly Ile Asn Asp Gly Ala Ala
             245                 250                 255

Met Val Val Met Lys Glu Ser Lys Ala Lys Glu Leu Gly Leu Lys
             260                 265                 270

Pro Met Ala Arg Leu Val Ala Phe Ala Ser Ala Gly Val Asp Pro Ala
             275                 280                 285

Ile Met Gly Thr Gly Pro Ile Pro Ala Ser Thr Lys Cys Leu Glu Lys
 290                 295                 300

Ala Gly Trp Thr Pro Ala Asp Leu Asp Leu Ile Glu Ala Asn Glu Ala
305                 310                 315                 320

Phe Ala Ala Gln Ala Met Ser Val Asn Gln Asp Met Gly Trp Asp Leu
             325                 330                 335

Ser Lys Val Asn Val Asn Gly Gly Ala Ile Ala Ile Gly His Pro Gly
             340                 345                 350

Ala Ser Gly Ala Arg Val Leu Val Thr Leu Leu Tyr Glu Met Gln Lys
             355                 360                 365

Arg Asp Ala Lys Lys Gly Leu Ala Thr Leu Cys Ile Gly Gly Gly Gln
 370                 375                 380

Gly Val Ala Leu Ala Val Val Glu Arg Met
```

385             390

(2) INFORMATION FOR SEQ ID NO:3:

(i) SEQUENCE CHARACTERISTICS:
        (A) LENGTH: 357 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:3:

```
Met Ser Asn Thr Asn Phe Phe Asn Asp Asp Trp Leu Glu Leu Gln Arg
1               5                   10                  15

Lys Tyr Trp Asp Asn Trp Thr Asp Met Ser Arg Lys Ala Met Gly Leu
            20                  25                  30

Asp Ser Ala Ser Ser Ser Ala Thr Thr Pro Trp Glu Ala Ala Ile Asp
        35                  40                  45

Gln Trp Trp Lys Ala Met Ala Pro Ala Pro Asp Leu Ser Arg Ser
50                  55                  60

Phe Met Glu Lys Met Met Glu Gln Gly Lys Asn Phe Phe Arg Leu Ala
65                  70                  75                  80

Asp Thr Phe Ala Lys Arg Ala Asp Glu Gly Asn Ala Gly Asn Gly Leu
                85                  90                  95

Glu Leu Trp Thr Lys Thr Leu Glu Asp Met Gln Lys Arg Phe Ser Gly
            100                 105                 110

Ser Leu Asp Asp Gly Gly Asn Thr Met Gln Arg Leu Met Ser Phe Trp
        115                 120                 125

Glu Leu Pro Leu Asp Asn Trp Gln Arg Met Met Ser Ser Met Ser Pro
130                 135                 140

Met Pro Gly Asp Met Leu Arg Asn Met Pro His Glu Gln Phe Lys Asp
145                 150                 155                 160

Ser Leu Asp Arg Ala Leu Ser Ala Pro Gly Leu Gly Tyr Thr Arg Glu
                165                 170                 175

Glu Gln Ser Gln Tyr Gln Glu Leu Met Arg Ser Ala Met Glu Tyr Gln
            180                 185                 190

Ala Ala Leu Gln Glu Tyr Thr Asn Val Tyr Thr Lys Leu Gly Met Lys
        195                 200                 205

Ser Val Glu His Met Gly Ser Tyr Ile Gln Gly Val Ile Asp Ser Gly
210                 215                 220

Lys Thr Ile Asp Ser Ala Arg Ala Leu Tyr Asp Asn Trp Val Ala Cys
225                 230                 235                 240

Cys Glu Gly Ala Tyr Ala Asp Glu Val Ala Thr Pro Glu Tyr Ala Arg
                245                 250                 255

Ile His Gly Arg Leu Val Asn Ala Gln Met Ala Leu Lys Lys Arg Met
            260                 265                 270

Ser Ile Leu Val Asp Glu Asn Leu Gly Ala Leu Asn Met Pro Thr Arg
        275                 280                 285

Ser Glu Leu Pro Thr Leu Gln Asp Arg Leu Gln Glu Thr Arg Arg Glu
290                 295                 300

Asn Lys Ala Leu Arg His Ser Leu Arg Asp Leu Glu Arg Arg Val Ala
305                 310                 315                 320

Ala Leu Ala Gly Glu Glu Pro Ala Thr Lys Pro Ala Thr Ala Leu Arg
                325                 330                 335
```

```
Ser Pro Ala Pro Ala Ala Lys Ala Pro Ala Arg Arg Thr Thr Lys
            340                 345                 350
Thr Asn Pro Ala Asp
        355
```

(2) INFORMATION FOR SEQ ID NO:4:

(i) SEQUENCE CHARACTERISTICS:
        (A) LENGTH: 355 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:4:

```
Met Phe Pro Ile Asp Ile Arg Pro Asp Lys Leu Thr Gln Glu Met Leu
1               5                   10                  15
Asp Tyr Ser Arg Lys Leu Gly Gln Gly Met Glu Asn Leu Leu Asn Ala
            20                  25                  30
Glu Ala Ile Asp Thr Gly Val Ser Pro Lys Gln Ala Val Tyr Ser Glu
        35                  40                  45
Asp Lys Leu Val Leu Tyr Arg Tyr Asp Arg Pro Glu Gly Ala Pro Glu
50                  55                  60
Ala Gln Pro Val Pro Leu Leu Ile Val Tyr Ala Leu Val Asn Arg Pro
65                  70                  75                  80
Tyr Met Thr Asp Ile Gln Glu Asp Arg Ser Thr Ile Lys Gly Leu Leu
            85                  90                  95
Ala Thr Gly Tyr Asp Val Tyr Leu Ile Asp Trp Gly Tyr Pro Asp Gln
            100                 105                 110
Ala Asp Arg Ala Leu Thr Leu Asp Tyr Ile Asn Gly Tyr Ile Asp
            115                 120                 125
Arg Cys Val Asp Tyr Leu Arg Glu Ala His Gly Val Asp Lys Val Asn
130                 135                 140
Leu Leu Gly Ile Cys Gln Gly Gly Ala Phe Ser Leu Met Tyr Ser Ala
145                 150                 155                 160
Leu His Pro Asp Lys Val Arg Asn Leu Val Thr Met Val Thr Pro Val
            165                 170                 175
Asp Phe Lys Thr Pro Asp Asn Leu Leu Ser Ala Trp Val Gln Asn Val
            180                 185                 190
Asp Ile Asp Leu Ala Val Asp Thr Met Gly Asn Ile Pro Gly Glu Leu
            195                 200                 205
Leu Asn Trp Thr Phe Leu Ser Leu Lys Pro Phe Ser Leu Thr Gly Gln
            210                 215                 220
Lys Tyr Val Asn Met Val Asp Leu Leu Asp Asp Pro Asp Lys Val Lys
225                 230                 235                 240
Asn Phe Leu Arg Met Glu Lys Trp Ile Phe Asp Ser Pro Asp Gln Ala
            245                 250                 255
Gly Glu Thr Phe Arg Gln Phe Ile Lys Asp Phe Tyr Gln Asn Asn Gly
            260                 265                 270
Phe Leu Asn Gly Gly Val Val Leu Gly Gly Gln Glu Val Asp Leu Lys
            275                 280                 285
Asp Ile Thr Cys Pro Val Leu Asn Ile Phe Ala Leu Gln Asp His Leu
            290                 295                 300
```

```
Val Pro Pro Asp Ala Ser Arg Ala Leu Lys Gly Leu Thr Ser Ser Pro
305                 310                 315                 320

Asp Tyr Thr Glu Leu Ala Phe Pro Gly Gly His Ile Gly Ile Tyr Val
            325                 330                 335

Ser Gly Lys Ala Gln Lys Glu Val Thr Pro Ala Ile Gly Lys Trp Leu
            340                 345                 350

Asn Glu Arg
        355
```

(2) INFORMATION FOR SEQ ID NO:5:

(i) SEQUENCE CHARACTERISTICS:
        (A) LENGTH: 356 amino acids
        (B) TYPE: amino acid
        (D) TOPOLOGY: linear (ii) MOLECULE TYPE: protein (vi) ORIGINAL SOURCE:
        (A) ORGANISM: Alcaligenes eutrophus (xi) SEQUENCE DESCRIPTION: SEQ ID NO:5:

```
Glu Ser Gly Gly Glu Ser Leu Arg Ala Gly Val Arg Asn Met Met Glu
1               5                   10                  15

Asp Leu Thr Arg Gly Lys Ile Ser Gln Thr Asp Glu Ser Ala Phe Glu
            20                  25                  30

Val Gly Arg Asn Val Ala Val Thr Glu Gly Ala Val Val Phe Glu Asn
            35                  40                  45

Glu Tyr Phe Gln Leu Leu Gln Tyr Lys Pro Leu Thr Asp Lys Val His
    50                  55                  60

Ala Arg Pro Leu Leu Met Val Pro Pro Cys Ile Asn Lys Tyr Tyr Ile
65                  70                  75                  80

Leu Asp Leu Gln Pro Glu Ser Ser Leu Val Arg His Val Val Glu Gln
                85                  90                  95

Gly His Thr Val Phe Leu Val Ser Trp Arg Asn Pro Asp Ala Ser Met
                100                 105                 110

Ala Gly Ser Thr Trp Asp Asp Tyr Ile Glu His Ala Ala Ile Arg Ala
            115                 120                 125

Ile Glu Val Ala Arg Asp Ile Ser Gly Gln Asp Lys Ile Asn Val Leu
            130                 135                 140

Gly Phe Cys Val Gly Gly Thr Ile Val Ser Thr Ala Leu Ala Val Leu
145                 150                 155                 160

Ala Ala Arg Gly Glu His Pro Ala Ala Ser Val Thr Leu Leu Thr Thr
            165                 170                 175

Leu Leu Asp Phe Ala Asp Thr Gly Ile Leu Asp Val Phe Val Asp Glu
            180                 185                 190

Gly His Val Gln Leu Arg Glu Ala Thr Leu Gly Gly Gly Ala Gly Ala
            195                 200                 205

Pro Cys Ala Leu Leu Arg Gly Leu Glu Leu Ala Asn Thr Phe Ser Phe
    210                 215                 220

Leu Arg Pro Asn Asp Leu Val Trp Asn Tyr Val Val Asp Asn Tyr Leu
225                 230                 235                 240

Lys Gly Asn Thr Pro Val Pro Phe Asp Leu Leu Phe Trp Asn Gly Asp
            245                 250                 255

Ala Thr Asn Leu Pro Gly Pro Trp Tyr Cys Trp Tyr Leu Arg His Thr
            260                 265                 270

Tyr Leu Gln Asn Glu Leu Lys Val Pro Gly Lys Leu Thr Val Cys Gly
```

```
                    275                 280                 285
Val Pro Val Asp Leu Ala Ser Ile Asp Val Pro Thr Tyr Ile Tyr Gly
    290                 295                 300

Ser Arg Glu Asp His Ile Val Pro Trp Thr Ala Ala Tyr Ala Ser Thr
305                 310                 315                 320

Ala Leu Leu Ala Asn Lys Leu Arg Phe Val Leu Gly Ala Ser Gly His
                325                 330                 335

Ile Ala Gly Val Ile Asn Pro Pro Ala Lys Asn Lys Arg Ser His Trp
                340                 345                 350

Thr Asn Asp Ala
            355
```

(2) INFORMATION FOR SEQ ID NO:6:

(i) SEQUENCE CHARACTERISTICS:
        (A) LENGTH: 351 amino acids
        (B) TYPE: amino acid
        (D) TOPOLOGY: linear (ii) MOLECULE TYPE: protein (vi) ORIGINAL SOURCE:
        (A) ORGANISM: Pseudomonas oleovorans (xi) SEQUENCE DESCRIPTION: SEQ ID NO:6:

```
Glu Thr Gly Gly Lys Ser Leu Leu Asp Gly Leu Ser Asn Leu Ala Lys
1               5                   10                  15

Asp Leu Val Asn Asn Gly Gly Met Pro Ser Gln Val Asn Met Asp Ala
                20                  25                  30

Phe Glu Val Gly Lys Asn Leu Gly Thr Ser Glu Gly Ala Val Val Tyr
                35                  40                  45

Arg Asn Asp Val Leu Glu Leu Ile Gln Tyr Lys Pro Ile Thr Glu Gln
50                  55                  60

Val His Ala Arg Pro Leu Leu Ile Val Pro Pro Gln Ile Asn Lys Phe
65                  70                  75                  80

Tyr Val Phe Asp Leu Ser Pro Glu Lys Ser Leu Ala Arg Tyr Cys Leu
                85                  90                  95

Arg Ser Gln Gln Gln Thr Phe Ile Thr Ser Trp Arg Asn Pro Thr Lys
                100                 105                 110

Ala Gln Arg Glu Trp Gly Leu Ser Thr Tyr Ile Asp Ala Leu Lys Glu
                115                 120                 125

Ala Val Asp Ala Val Leu Ala Ile Thr Gly Ser Lys Asp Leu Asn Met
                130                 135                 140

Leu Gly Ala Cys Ser Gly Gly Ile Thr Cys Thr Ala Leu Val Gly His
145                 150                 155                 160

Tyr Ala Ala Leu Gly Glu Asn Lys Val Asn Ala Leu Thr Leu Leu Val
                165                 170                 175

Ser Val Leu Asp Thr Thr Met Asp Asn Gln Val Ala Leu Phe Val Asp
                180                 185                 190

Glu Gln Thr Leu Glu Ala Ala Lys Arg His Ser Tyr Gln Ala Gly Val
                195                 200                 205

Leu Glu Gly Ser Glu Met Ala Lys Val Phe Ala Trp Met Arg Pro Asn
                210                 215                 220

Asp Leu Ile Trp Asn Tyr Trp Val Asn Asn Tyr Leu Leu Gly Asn Glu
225                 230                 235                 240

Pro Pro Val Phe Asp Ile Leu Phe Trp Asn Asn Asp Thr Thr Arg Leu
                245                 250                 255
```

```
Pro Ala Ala Phe His Gly Asp Leu Ile Glu Met Phe Lys Ser Asn Pro
                260                 265                 270

Leu Thr Arg Pro Asp Ala Leu Glu Val Cys Gly Thr Pro Ile Asp Leu
            275                 280                 285

Lys Gln Val Lys Cys Asp Ile Tyr Ser Leu Ala Gly Thr Asn Asp His
        290                 295                 300

Ile Thr Pro Trp Gln Ser Cys Tyr Arg Ser Ala His Leu Phe Gly Gly
305                 310                 315                 320

Lys Ile Glu Phe Val Leu Ser Asn Ser Gly His Ile Gln Ser Ile Leu
                325                 330                 335

Asn Pro Pro Gly Asn Pro Lys Ala Arg Phe Met Thr Gly Ala Asp
                340                 345                 350
```

(2) INFORMATION FOR SEQ ID NO:7:

(i) SEQUENCE CHARACTERISTICS:
        (A) LENGTH: 352 amino acids
        (B) TYPE: amino acid
        (D) TOPOLOGY: linear (ii) MOLECULE TYPE: protein (vi) ORIGINAL SOURCE:
        (A) ORGANISM: Pseudomonas oleovorans (xi) SEQUENCE DESCRIPTION: SEQ ID NO:7:

```
Asn Ser Gly Gly Gln Ser Leu Val Phe Gly Val Ala His Leu Leu Asp
1               5                   10                  15

Asp Leu Arg His Asn Asp Gly Leu Pro Arg Gln Val Asp Glu Arg Ala
            20                  25                  30

Phe Glu Val Gly Gly Asn Leu Ala Ala Thr Ala Gly Ala Val Val Phe
        35                  40                  45

Arg Asn Glu Leu Leu Glu Leu Ile Gln Tyr Lys Arg Met Ser Glu Lys
50                  55                  60

Gln His Ala Arg Pro Leu Leu Val Pro Pro Gln Ile Asn Lys Phe
65              70                  75                  80

Tyr Ile Phe Asp Leu Ser Ser Thr Asn Ser Phe Val Gln Tyr Met Leu
                85                  90                  95

Lys Asn Gly Leu Gln Val Phe Met Val Ser Trp Arg Asn Pro Asp Pro
                100                 105                 110

Arg His Arg Glu Trp Gly Leu Ser Ser Tyr Val Gln Ala Leu Glu Glu
            115                 120                 125

Ala Leu Asn Ala Cys Arg Ser Ile Ser Gly Asn Arg Asp Pro Asn Leu
130                 135                 140

Met Gly Ala Cys Ala Gly Gly Leu Thr Met Ala Ala Leu Gln Gly His
145                 150                 155                 160

Leu Gln Ala Lys His Gln Leu Arg Arg Val Arg Ser Ala Thr Tyr Leu
                165                 170                 175

Val Ser Leu Leu Asp Ser Lys Phe Glu Ser Pro Ala Ser Leu Phe Ala
            180                 185                 190

Asp Glu Gln Thr Ile Glu Ala Ala Lys Arg Arg Ser Tyr Gln Arg Gly
        195                 200                 205

Val Leu Asp Gly Ala Glu Val Ala Arg Ile Phe Ala Trp Met Arg Pro
    210                 215                 220

Asn Asp Leu Ile Trp Asn Tyr Trp Val Asn Asn Tyr Leu Leu Gly Lys
225                 230                 235                 240
```

```
Thr Pro Pro Ala Phe Asp Ile Leu Tyr Trp Asn Ala Asp Ser Thr Arg
            245                 250                 255

Leu Pro Ala Ala Leu His Gly Asp Leu Leu Asp Phe Phe Lys Leu Asn
            260                 265                 270

Pro Leu Thr His Pro Ala Gly Leu Glu Val Cys Gly Thr Pro Ile Asp
            275                 280                 285

Leu Gln Lys Val Glu Leu Asp Ser Phe Thr Val Ala Gly Ser Asn Asp
    290                 295                 300

His Ile Thr Pro Trp Asp Ala Val Tyr Arg Ser Ala Leu Leu Leu Gly
305                 310                 315                 320

Gly Asp Arg Arg Phe Val Leu Ala Asn Ser Gly His Ile Gln Ser Ile
                325                 330                 335

Ile Asn Pro Pro Gly Asn Pro Lys Ala Tyr Tyr Leu Ala Asn Pro Lys
            340                 345                 350
```

(2) INFORMATION FOR SEQ ID NO:8:

(i) SEQUENCE CHARACTERISTICS:
        (A) LENGTH: 6977 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Chromatium vinosum (xi) SEQUENCE DESCRIPTION: SEQ ID NO:8:

```
GCTTAAGTAG GTCCCGGTGA TAGAGGTTGA CGGCTCAAGC CTGAACTTGA AGCTAAAGGT      60

CTGGGACAGT GTACTTTGGG CTATCAGACG AGTACTCATG CCGCGAAGTG TGCCCTGCCG     120

ACTAGGACTG AGGTAGGCTA GGCGTAGAGC GCGGCCTACA GCTAAACAAC TAGCTTCCTG     180

ACTCGGCCGG ACCTAAGGAC TCACGAGGTA ACTAGGACCT CTTAGGTGTC GGCCCCCGCC     240

CGCTGGCTCG GAAACGCTGA CCGCGGCCGA AGGACTCAGA TGACTGGAAA CGGCCGACGC     300

GGCAGGCCTA AGCGCTACTG CAGTCTCGCC CCGCAAAGAC CGTATAAGCG TAGGGCGGTC     360

AGTCAGTCGT AGGTTCCAAC TACCAACCGG CATTGTGCGC GGGTGGGGCT ACACAGCCCA     420

CAGCGCGCGG GGACAGCCCG ACCGCGCGCG ACCACCTTGT GACCCGGTGC GTAGGCGTAC     480

GGCCGCACGT TACAGGCCGG ACGCCGCTCT GTGCAGGCGG GACCGAGACC CTGACCTTTG     540

TCGTTCCTCC TAAGCCTGCG CGGAAGCACG TCTAGCTTCT CCAGAAAGGC CCACTCCGTC     600

ACGGCTGCGG CTACAAGAAG CTCGTCGAGT AAGCCCAGTC ACCCTAGCCG ACCGCTGTAA     660

AGATGTAGGT CCTAACTTAG TTCGGACCAT ATCCCCGCGG AATTGCACTT CCGGTCGAGG     720

TTCAGGCGAG CTACTCGCTG CTGCGGGCCA CTCAGGGCTC GCAGTAGCAC CTACGGCAAG     780

CTGCCGACTG CTGTCGCTCG GCGGCCTTAA CGAGGCCGCC GAGCCCTTCG CAATAGCGAG     840

CAACTCGGTG AATGGCTACC GGCCGCACTG AAGAAAGACG CGGAACGGCG ACTGTATCTA     900

CGGCTACACT GGCGGCCCCT TCCGGTCGAG CCACATCAGG CCCGACGACC AGTCAGGGAA     960

CTCGCGGGAT CTCCGTAGGC CGCCGTGGTC CACTAGGACC TCGCGCTTCT ACAACTCGTG    1020

GCCCGTCCAC TACAGGAAGT CCAGGTGAAG GACAGGCGGG TCGTGGTGCG GCGGTAACTC    1080

CTTCGGCAAC AAGACCATCT TCAGGAACTA CTTGACTGCC TTCCAGAGCG GCCGGACTAG    1140

GCCCGACAGC TTCTAGGTAA AGAGGTACGC GTCCTTCAAG AACTGGAACA GGCCCAGCAG    1200

CTCGTCTAGT TGGTACAACT GCATGAAGAC TGGGCAGTCC GACTTTCCGA ACTCGCTGTC    1260
```

```
CTTCCAGGTC AAGTCGTCGA GTGGCCCCTA CAACGGGTAC CACAGCTGGC GGTCTAGCTA    1320

CAGCTGCAAG ACGTGGGTCC GGCTCTCGTC CAACAGGCCC CAGAACTTCA GCTGGCCGCA    1380

CTGGTACCAG TGCTCCAACG CGTGGAACAG GCCCACGTCG CGCGACATGT AGTCCGACTT    1440

CCGCGGCGGG ACTGTCTATG GCTCGTCTAA CTGGAACAGC TGCGGCACCC GAAGCGCGTC    1500

TATCAGGTGC GTCGCCAGCT ACATCGGCAA CTACATCAGC AGCTCGCACT CGCGCGCCAG    1560

CGGGACTAGG CCTATCGGGG TCAGCTAGTC CATCTGCAGG ACCGGCCACC GGTCGTCAGG    1620

GAACTACCAC CTCGCCAGAA GGACCTACAG CCAGTACATC CCGGCCAACT GGTCCCGCAT    1680

CTGCTAGTCC TCGCCGTGCC CGACCCGAAG CCCGCGCGGG AGCCCAGCCA GTATCGCTAT    1740

CTCCTGGTCG AACAGGAGCG ACATCTGCCG GACGAACCCC GACTGCGGCC ACAGCTACCG    1800

GAGCCGCAAC TCGTCTAAGA GGTACGGGAC TGGGTCGAAC GCCGACATCA GCTCGTAGAG    1860

GACCCACTCA AACAGGCCGG CCTACAGCTA CCCCTTGTAC TAGCGACAGG AGACTAAGAC    1920

AGACCACTCG GACGACAAGC TAGTCGGCGA ACTGCGAGTT AGCCGGCCTA ACCAGAACCA    1980

CCACGCGGCC GCACGGCCTC GGAACCGCCG GCCCCGCCCG CTGGACTCGC GTCACCGTCC    2040

GAACCACCGG CCGAGGAGTG GCCGGTCCCG ACGCTGCGCT GCAAGGTCTA GCGCGTCCGA    2100

CACTGCGTCC CGGAACAAGA GCGCTGCCCA GAGGACCTCG GCCAGGACCT CCCACGCGTC    2160

GAGCGACGCC CAGCCGTACA AGTTACGCGG GTCCAAGAGC AGCTGGTCCT AGCTGTACGC    2220

GAAGAACTCG CGGTAGACTC GCAACTGGTC GGCCGGCACC TACGCCCGCA TAAGGCCACA    2280

CCGCTGGAGC AGCCGTATCC GCGGAAGCGT CGTCCGCTGG GTCAACAGCA TCTCGCGCGC    2340

GCGGCTCAGC TACCAAAACG CGACAGCTA CTGTGGGACC TACATCCTCG GGTACACGAG    2400

CTGGCTGAAG TACGGCTCGA ACCACATCTG CAACCACATA AGGACCTCGC GCCGGACTAT    2460

GAGGTACCGC GACGCGTAGT CGAGGACTAT GACCGAGACG AGGAGCGCCC ACATCGGCTC    2520

TGGCCCGCGG CTCTCCCGAG CTAGTTCTGA CAGGAACTTG ACGAGCACCC CGTACAACGC    2580

GTCGTACAGC GGGCCGTAGC CGCTGTAGCT CCTGTAGTAC GCGACGGTCA ACAGCTCGCC    2640

GTCGAGGGTC TTGCTGTAGT CCGCGACGTA CCACAACGGC GGCAGCAGCT CGCTCGGCGA    2700

CTTCGCGAAG ACGTACAGAA GCTCGCAGAA CCAGGTCTCG AGGTTCGGCA ACGGCCGCAA    2760

CGGGAGCAGC CGCGCAAACC GCTTCCACAG CCGCTCTGCC TTCTTCAAGA ACGGGACGAG    2820

GTAGTAGAAA AGGTACTTGC TCGCACTGTC TAGGCCCCGC CGCCCGCGGT ACCGAAAGGT    2880

GGTGACTAGC TACCGGCGGA GGGTCCCGCA CAACCGGCTT GACCTCCGCG ACAGGTCTGG    2940

GTACCGGAAC GCCGAGTACA GCCAGGTCAA CAGGGTCATG AACGCAACGT CAAGCTCGGT    3000

TAGCAGTAAC TTCTTTAATC ACAACGAGTA CCTGCATGGG AGGAGCACCG CGCACCACAA    3060

CCCGCTTGCC ATAGTACACC TAAACACGTG ACGTTGTTTC TACGCTTCTT AGGTGTCCGG    3120

CGCTGGGGTA TAGCCCCTGC GAGCAGGTAA AGGTTAGTCT TAGGTCTCCT GTAGGTGCGG    3180

TACTCGCTCT TGTAGCAGTA CGTCGACGCC GGCCGCAGTG CCATCGGAAC CTTCGGCGGC    3240

AGTCTGTCGT CACTCTCGGC CACCGAGATC GGCACCGCCG TGCTCAAGGG GCTGCTGGCG    3300

CGTACCGGAC TCGCGCCGGA ACAGATCGAC GAGGTGATTC TCGCCAGGT GCTGACCGCC    3360

GGCGTGGGCC AGAACCCCGC CCGTCAGACC ACGCTGCACG CGGGGCTACC GCATTCGGTG    3420

CCGGCCATGA CCATCAACAA GGTCTGCGGC AGCGGTCTGA AGGCGGTGCA TCTGGCGATG    3480

CAGGCCATCG CCTGCGGGGA TGCCGACATC GTCATCGCCG GCGGTCAGGA GAGCATGAGC    3540

CAGTCCTCGC ACGTCCTGCC GCGTTCGCGC GACGGTCAGC GCATGGGCGA CTGGTCGATG    3600

AAGGACACCA TGATCGTCGA CGGCCTCTGG GATGCCTTCA ACAACTATCA CATGGGCACC    3660
```

```
ACCGCCGAGA ACATCGCCCA GAAGTACGGC TTTACGCGCG AGCAGCAGGA CGCCTTCGCC      3720

GCCGCCTCGC AGCAGAAGAC CGAGGCCGCG CAGAAGGCTG GCCGCTTCCA GGACGAGATC      3780

ATTCCGATCG AGATTCCGCA GCGCAAGGGC GATCCGAAGG TGTTTGATGC CGACGAGTTC      3840

CCGCGTCACG GCACCACGGC CGAGAGTCTG GGCAAGCTGC GTCCGGCCTT CTCGAAGGAC      3900

GGCAGCGTCA CGGCGGGTAA CGCCTCCGGC ATCAACGACG GGCGGCCAT GGTCGTGGTG       3960

ATGAAGGAGT CCAAGGCCAA GGAACTGGGT CTGAAGCCGA TGGCGCGTCT GGTGGCCTTC      4020

GCCAGCGCCG GTGTCGATCC GGCGATCATG GGGACGGGCC CGATCCCGGC GTCGACCAAG      4080

TGCCTGGAGA AGGCCGGCTG GACCCCGGCG GATCTGGATC TGATCGAGGC CAACGAAGCC      4140

TTCGCCGCGC AGGCCATGTC GGTCAACCAG GACATGGGCT GGGATCTGTC CAAGGTCAAC      4200

GTCAACGGCG GCGCCATCGC CATCGGTCAT CCGATCGGCG CCTCCGGTGC GCGCGTGCTC      4260

GTGACCCTGC TCTATGAGAT GCAGAAGCGC GACGCCAAGA AGGGTCTGGC GACGCTGTGC      4320

ATCGGCGGCG GCCAGGGCGT GGCGCTGGCG GTCGAGCGGA TGTGAGCCGT CGTCCGCCGG      4380

TCTGAATCGC CGGCGGACCG AGCCTCCTGA ATCGCTCCAG GCACTGAACG CCCTGCCGAT      4440

CCCGGATCGG TGGGGCGTTT GCGCGCTTGG GGTAGACTTG CCGAACGACC AGCCGAACCG      4500

CCCGGGTGCC CATGAACAGC GAGCGCATCA TCAAGAAGTA TCCGAACCGC CGCCTCTACG      4560

ACACCGAGGT CAGCCGCTAT ATCACCCTCG CCGATGTGCG CGATCTGGTG ATGAGCGGAC      4620

AGCCCTTCCG CGTCCTCGAC AGCGCCAATG ACAGCGATAT CACCCGTTCC ATCCTGCTCC      4680

AGATCATGCT GGAGGAGGAG ACCGGCGGTC AGCCGCTGTT CAGCGCCAAC ATGCTGGCCC      4740

AGATCATCCG CTTCTACGGC GGCACCCTTC AGGGCACCTT CGCCCGCTAT CTGGAATCTT      4800

CACTCGACCT GTTCGCCAAG CAGCAACAGG AAGTGACCAA GGCACTCACC GACAATCCCT      4860

TCGGACGGT GACACGCCTG ACTCAGAAGA ACGTCGAGAT CTGGGCTGAT CTCCAGGACG       4920

AACTCATGCG CGCGGCTGGC TTTCCGGTCG CGCCGCGCAA GAAAAAAGAA TAATGAGGAT      4980

TGCGAAAATT GCGCTTGACG GCCGTCGGTC ACAGCTTTAT TGTGCAATGC AACATTGCTG      5040

CACTGCACAA ACCTTACGGA GAGATGATCA TGAACACCAC CGACAGCCTC AAGACCGTCA      5100

ACGAGTGGAC CAACAAGAGC GTCGAGCGCA TGACCAGCTT CGGTGAGCTG AACGTGCGTC      5160

TGTTCGAGAA GCTGGCCGCC CGTCAGATGG ACGCCGTGAA CCTGTACATG GATCACAGCA      5220

TGCGCCTGAT GAAGCTGGCC ACCGAGTCCA AGGGTTACAA TGACCTCTTC AAGGGTCAGG      5280

TCGACGCCAC CAAGGAACTG AGCGAGCGCG TCATGGCCGA GAGCAAGGCC ACCATGCAGT      5340

TCTTCGGCGA TGCCCGCGAC GAATACCGCG TGTGGTTCGA GAAGAGCCTG AACGACGTCA      5400

GCGAAGATCT GCGCAAGAGC GTCGCCGTCT AAAGACGCCG ACCTCTGGGC CATCGCGATC      5460

CAGGGATGGA TCGCCATTGG TCATGCTTCC GGATCGGCCG GGAGCACGCC CAATGGAACC      5520

AACGCTTCAC CTTGCCTGCC GCTTGGTAGT AAAGTGGCCT TGAAGTTCGA CGACACTGTT      5580

CATCGTTCTC AATAGTTCCA AAGATTCCTG GAGGAACCCC ATGGCTCGTA TCGCACTCGT      5640

CACCGGCGG ATCGGCGGCA TCGGCACTTC GATCTGCACA CGCCTGGCAA AGGATGGCTG       5700

CACCGTCGTG GCGAACTGCC ATCCGTCCGA GGCGGCCGCC GCCGAAGAGT GGAAGCAGGC      5760

CCGTGCCGCC GAGGGGTTCG ACATCGCCGT CTTCACCGCT GACGTGTCCT CGTTCGACGA      5820

CAGCGCGCGC ATGGTTCGCG AGATCACAGA GCAGGTCGGT CCCATCGACA TCCTGGTCAA      5880

CTGTGCCGGC ATCACCCGCG ACAAGACCTT CAAGAAGATG GAGCAGGCGC ACTGGGAGGC      5940

CGTGATCAAC GTCAACCTCA ACAGCGTCTT CAACGTCACC CGTCAGGTGT GGGACGGGAT      6000
```

-continued

```
GCTGGAGCGC GGCTTCGGGC GTATCATCAA CATCTCGTCG GTCAACGGTC AGCGCGGCCA       6060

CTTCGGTCAG GCCAACTATT CCGCCGCCAA GGCCGGTATG CACGGCTTCA CCATGGCTCT       6120

GGCTCAGGAG GGTGCGTCCA AGGGCGTGAC CGTCAACACC ATCTCGCCCG GCTATGTCGA       6180

GACGGCCATG ACCCTGGCGA TGAACGACGA TGTGCGCAAC AGCATCATCA GCGGTATTCC       6240

GATGCGTCGC ATGGCTCAGC CTAATGAGAT CGCCGCCGCC ATCGCTTTCC TGGCCGGCGA       6300

CGAGAGCGGT TATATGACGG GCGCCAATCT GCCGGTCAAC GGCGGTCTGT TCATGCATTG       6360

ATTTAGATCA TACCGGGCCG AATACAAAAC ACTGACAATG GCCCGGTGTT TCAGGATCTC       6420

ACCGAGTCCT CCTCGTCTCT CTCATCATGA ACGTTTACA GCCCGGCGCC AGCCGGGCTT        6480

TTTTTTGTGT AGAATCGAAT CGCCCATCCG ATGAACGCTG TGATGACCGA CGTACGCGAT       6540

CTGATCCGCT ACTGCGATGA CGTGCTCGAC GCGGCGCGCT TCGCCGACTA TGCGCCGAAT       6600

GGTTTGCAAG TGGAGGGCGA ACGGCCGCTC CAGCGGCTGG TGTCGGGCGT GACGGCCAGC       6660

GCCGCGTTGA TCGAGGCCGC GATCGCGGAG CACGCCGACG CCATTCTGGT CCATCATGGC       6720

TGGTTCTGGA AGAACGAGAA TCCCTGCCTG ATCGGCATCA AGGGGCAGCG CGCAAGGACA       6780

TTGCTCAGCG CGGGTGTGAG TCTGATCGCC TATCATCTGC CGCTCGATGC CCATCCCGAA       6840

CTCGGCAACA ATGCCACACT CGGTCGCCGG CTCGATTTCA TCGACATGGA ACCGACCGCA       6900

CTGGCCAATG GTCTGCTGTG GGCGGCGATT GGCTCAGCCC ATGACGCCTG CGTCCTTCAC       6960

GGAGCATGTC TCGCATC                                                     6977
```

(2) INFORMATION FOR SEQ ID NO:9:

(i) SEQUENCE CHARACTERISTICS:
        (A) LENGTH: 246 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:9:

```
Met Ala Arg Ile Ala Leu Val Thr Gly Gly Ile Gly Gly Ile Gly Thr
1               5                   10                  15

Ser Ile Cys Thr Arg Leu Ala Lys Asp Gly Cys Thr Val Val Ala Asn
                20                  25                  30

Cys His Pro Ser Glu Ala Ala Ala Glu Glu Trp Lys Gln Ala Arg
            35                  40                  45

Ala Ala Glu Gly Phe Asp Ile Ala Val Phe Thr Ala Asp Val Ser Ser
        50                  55                  60

Phe Asp Asp Ser Ala Arg Met Val Arg Glu Ile Thr Glu Gln Val Gly
65                  70                  75                  80

Pro Ile Asp Ile Leu Val Asn Cys Ala Gly Ile Thr Arg Asp Lys Thr
                85                  90                  95

Phe Lys Lys Met Glu Gln Ala His Trp Glu Ala Val Ile Asn Val Asn
                100                 105                 110

Leu Asn Ser Asn Phe Asn Val Thr Arg Gln Val Trp Asp Gly Met Leu
            115                 120                 125

Glu Arg Gly Phe Gly Arg Ile Ile Asn Ile Ser Ser Val Asn Gly Gln
        130                 135                 140

Arg Gly Gln Phe Gly Gln Ala Asn Tyr Ser Ala Ala Lys Ala Gly Met
145                 150                 155                 160
```

```
His Gly Phe Thr Met Ala Leu Ala Gln Glu Gly Ala Ser Lys Gly Val
                165                 170                 175

Thr Val Asn Thr Ile Ser Pro Gly Tyr Val Glu Thr Ala Met Thr Leu
                180                 185                 190

Ala Met Asn Asp Asp Val Arg Asn Ser Ile Ile Ser Gly Ile Pro Met
                195                 200                 205

Arg Arg Met Ala Gln Pro Asn Glu Ile Ala Ala Ile Ala Phe Leu
                210                 215                 220

Ala Gly Asp Glu Ser Gly Tyr Met Thr Gly Ala Asn Leu Pro Val Asn
225                 230                 235                 240

Gly Gly Leu Phe Met His
                245

(2) INFORMATION FOR SEQ ID NO:10:

(i) SEQUENCE CHARACTERISTICS:
        (A) LENGTH: 153 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:10:

Met Asn Ser Glu Arg Ile Ile Lys Lys Tyr Pro Asn Arg Arg Leu Tyr
1               5                   10                  15

Asp Thr Glu Val Ser Arg Tyr Ile Thr Leu Ala Asp Val Arg Asp Leu
                20                  25                  30

Val Met Ser Gly Gln Pro Phe Arg Val Leu Asp Ser Ala Asn Asp Ser
                35                  40                  45

Asp Ile Thr Arg Ser Ile Leu Leu Gln Ile Met Leu Glu Glu Glu Glu
                50                  55                  60

Thr Gly Gly Gln Pro Leu Phe Ser Ala Asn Met Leu Ala Gln Ile Ile
65                  70                  75                  80

Arg Phe Tyr Gly Gly Thr Leu Gln Gly Thr Phe Ala Arg Tyr Leu Glu
                85                  90                  95

Ser Ser Leu Asp Leu Phe Ala Lys Gln Gln Gln Glu Val Thr Lys Ala
                100                 105                 110

Leu Thr Asp Asn Pro Phe Gly Thr Val Thr Arg Leu Thr Gln Lys Asn
                115                 120                 125

Val Glu Ile Trp Ala Asp Leu Gln Asp Glu Leu Met Arg Ala Ala Gly
                130                 135                 140

Phe Pro Val Ala Pro Arg Lys Lys Glu
145                 150

(2) INFORMATION FOR SEQ ID NO:11:

(i) SEQUENCE CHARACTERISTICS:
        (A) LENGTH: 120 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:11:

Met Asn Thr Thr Asp Ser Leu Lys Thr Val Asn Glu Trp Thr Asn Lys
```

```
1               5                   10                  15
Ser Val Glu Arg Met Thr Ser Phe Gly Glu Leu Asn Val Arg Leu Phe
                20                  25                  30

Glu Lys Leu Ala Ala Arg Gln Met Asp Ala Val Asn Leu Tyr Met Asp
            35                  40                  45

His Ser Met Arg Leu Met Lys Leu Ala Thr Glu Ser Lys Gly Tyr Asn
        50                  55                  60

Asp Leu Phe Lys Gly Gln Val Asp Ala Thr Lys Glu Leu Ser Glu Arg
65                  70                  75                  80

Val Met Ala Glu Ser Lys Ala Thr Met Gln Phe Phe Gly Asp Ala Arg
                85                  90                  95

Asp Glu Tyr Arg Val Trp Phe Asp Lys Ser Leu Asn Asp Val Ser Glu
            100                 105                 110

Asp Leu Arg Lys Ser Val Ala Val
        115                 120

(2) INFORMATION FOR SEQ ID NO:12:

(i) SEQUENCE CHARACTERISTICS:
        (A) LENGTH: 155 amino acids
        (B) TYPE: amino acid
        (D) TOPOLOGY: linear (ii) MOLECULE TYPE: protein (vi) ORIGINAL SOURCE:
        (A) ORGANISM: Chromatium vinosum (xi) SEQUENCE DESCRIPTION: SEQ ID NO:12:

Met Asn Ala Val Met Thr Asp Val Arg Asp Leu Ile Arg Tyr Cys Asp
1               5                   10                  15

Asp Val Leu Asp Ala Ala Arg Phe Ala Asp Tyr Ala Pro Asn Gly Leu
                20                  25                  30

Gln Val Glu Gly Glu Arg Pro Leu Gln Arg Leu Val Ser Gly Val Thr
            35                  40                  45

Ala Ser Ala Ala Leu Ile Glu Ala Ala Ile Ala Glu His Ala Asp Ala
        50                  55                  60

Ile Leu Val His His Gly Trp Phe Trp Lys Asn Glu Asn Pro Cys Leu
65                  70                  75                  80

Ile Gly Ile Lys Gly Gln Arg Ala Arg Thr Leu Leu Ser Ala Gly Val
                85                  90                  95

Ser Leu Ile Ala Tyr His Leu Pro Leu Asp Ala His Pro Glu Leu Gly
            100                 105                 110

Asn Asn Ala Thr Leu Gly Arg Arg Leu Asp Phe Ile Asp Met Glu Pro
        115                 120                 125

Thr Ala Leu Ala Asn Gly Leu Leu Trp Ala Ala Ile Gly Ser Ala His
        130                 135                 140

Asp Ala Cys Val Leu His Gly Ala Cys Leu Ala
145                 150                 155

(2) INFORMATION FOR SEQ ID NO:13:

(i) SEQUENCE CHARACTERISTICS:
        (A) LENGTH: 393 amino acids
        (B) TYPE: amino acid
        (D) TOPOLOGY: linear (ii) MOLECULE TYPE: protein (vi) ORIGINAL SOURCE:
```

(A) ORGANISM: Alcaligenes eutrophus (xi) SEQUENCE DESCRIPTION: SEQ ID NO:13:

```
Met Thr Asp Val Val Ile Ser Ala Ala Arg Thr Ala Val Gly Lys
 1               5                  10                  15

Phe Gly Gly Ser Leu Ala Lys Ile Pro Ala Pro Glu Leu Gly Ala Val
                20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
                100                 105                 110

Gly Gly Gln Glu Asn Met Ser Ala Ala Pro His Val Leu Pro Gly Ser
                115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
                180                 185                 190

Gly Lys Phe Asp Glu Glu Ile Val Pro Val Leu Ile Pro Gln Arg Lys
                195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
                260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
                340                 345                 350

Ala Ser Gly Cys Arg Ile Leu Val Thr Leu Leu His Glu Met Lys Arg
                355                 360                 365

Arg Asp Ala Lys Lys Gly Leu Ala Ser Leu Cys Ile Gly Gly Gly Met
    370                 375                 380

Gly Val Ala Leu Ala Val Glu Arg Lys
385                 390
```

(2) INFORMATION FOR SEQ ID NO:14:

(i) SEQUENCE CHARACTERISTICS:
        (A) LENGTH: 391 amino acids
        (B) TYPE: amino acid
        (D) TOPOLOGY: linear (ii) MOLECULE TYPE: protein (vi) ORIGINAL SOURCE:
        (A) ORGANISM: Zoogloea ramigera (xi) SEQUENCE DESCRIPTION: SEQ ID NO:14:

```
Met Ser Thr Pro Ser Ile Val Ile Ala Ser Ala Arg Thr Ala Val Gly
1               5                   10                  15

Ser Phe Asn Gly Ala Phe Ala Asn Thr Pro Ala His Glu Leu Gly Ala
            20                  25                  30

Thr Val Ile Ser Ala Val Leu Glu Arg Ala Gly Val Ala Ala Gly Glu
        35                  40                  45

Val Asn Glu Val Ile Leu Gly Gln Val Leu Pro Ala Gly Glu Gly Gln
    50                  55                  60

Asn Pro Ala Arg Gln Ala Ala Met Lys Ala Gly Val Pro Gln Glu Ala
65                  70                  75                  80

Thr Ala Trp Gly Met Asn Gln Leu Cys Gly Ser Gly Leu Arg Ala Val
                85                  90                  95

Ala Leu Gly Met Gln Gln Ile Ala Thr Gly Asp Ala Ser Ile Ile Val
            100                 105                 110

Ala Gly Gly Met Glu Ser Met Ser Met Ala Pro His Cys Ala His Leu
        115                 120                 125

Ala Gly Val Lys Met Gly Asp Phe Lys Met Ile Asp Thr Met Ile Lys
    130                 135                 140

Asp Gly Leu Thr Asp Ala Phe Tyr Gly Tyr His Met Gly Thr Thr Ala
145                 150                 155                 160

Glu Asn Val Ala Lys Gln Trp Gln Leu Ser Arg Asp Glu Gln Asp Ala
                165                 170                 175

Phe Ala Val Ala Ser Gln Asn Lys Ala Glu Ala Ala Lys Lys Asp Gly
            180                 185                 190

Arg Phe Lys Asp Glu Ile Val Pro Phe Ile Val Lys Gly Arg Lys Gly
        195                 200                 205

Asp Ile Thr Val Asp Ala Asp Glu Tyr Ile Arg His Gly Ala Thr Leu
    210                 215                 220

Asp Ser Met Ala Lys Leu Arg Pro Ala Phe Asp Lys Glu Gly Thr Val
225                 230                 235                 240

Thr Ala Gly Asn Ala Ser Gly Leu Asn Asp Gly Ala Ala Ala Ala Leu
                245                 250                 255

Leu Met Ser Glu Ala Glu Ala Ser Arg Arg Gly Ile Gln Pro Leu Gly
            260                 265                 270

Arg Ile Val Ser Trp Ala Thr Val Gly Val Asp Pro Lys Val Met Gly
        275                 280                 285

Thr Gly Pro Ile Pro Ala Ser Arg Lys Ala Leu Glu Arg Ala Gly Trp
    290                 295                 300

Lys Ile Gly Asp Leu Asp Leu Val Glu Ala Asn Glu Ala Phe Ala Ala
305                 310                 315                 320

Gln Ala Cys Ala Val Asn Lys Asp Leu Gly Trp Asp Pro Ser Ile Val
                325                 330                 335

Asn Val Asn Gly Gly Ala Ile Ala Ile Gly His Pro Ile Gly Ala Ser
```

```
                    340                 345                 350
Gly Ala Arg Ile Leu Asn Thr Leu Leu Phe Glu Met Lys Arg Arg Gly
            355                 360                 365
Ala Arg Lys Gly Leu Ala Thr Leu Cys Ile Gly Gly Met Gly Val
    370                 375                 380
Ala Met Cys Ile Glu Ser Leu
385                 390

(2) INFORMATION FOR SEQ ID NO:15:

(i) SEQUENCE CHARACTERISTICS:
         (A) LENGTH: 388 amino acids
         (B) TYPE: amino acid
         (D) TOPOLOGY: linear (ii) MOLECULE TYPE: protein (vi) ORIGINAL SOURCE:
         (A) ORGANISM: Escherichia coli (xi) SEQUENCE DESCRIPTION: SEQ ID NO:15:

Met Glu Gln Val Val Ile Val Asp Ala Ile Arg Thr Pro Met Gly Arg
1               5                   10                  15
Ser Lys Gly Gly Ala Phe Arg Asn Val Arg Ala Glu Asp Leu Ser Ala
            20                  25                  30
His Leu Met Arg Ser Leu Leu Ala Arg Asn Pro Ala Leu Glu Ala Ala
        35                  40                  45
Ala Leu Asp Asp Ile Tyr Trp Gly Cys Val Gln Gln Thr Leu Glu Gln
    50                  55                  60
Gly Phe Asn Ile Ala Arg Asn Ala Ala Leu Leu Ala Glu Val Pro His
65                  70                  75                  80
Ser Val Pro Ala Val Thr Val Asn Arg Leu Cys Gly Ser Ser Met Gln
                85                  90                  95
Ala Leu His Asp Ala Ala Arg Met Ile Met Thr Gly Asp Ala Gln Ala
            100                 105                 110
Cys Leu Val Gly Gly Val Glu His Met Gly His Val Pro Met Ser His
        115                 120                 125
Gly Val Asp Phe His Pro Gly Leu Ser Arg Asn Val Ala Lys Ala Ala
    130                 135                 140
Gly Met Met Gly Leu Thr Ala Glu Met Leu Ala Arg Met His Gly Ile
145                 150                 155                 160
Ser Arg Glu Met Gln Asp Ala Phe Ala Ala Arg Ser His Ala Arg Ala
                165                 170                 175
Trp Ala Ala Thr Gln Ser Ala Ala Phe Lys Asn Glu Ile Ile Pro Thr
            180                 185                 190
Gly Gly His Asp Ala Asp Gly Val Leu Lys Gln Phe Asn Tyr Asp Glu
        195                 200                 205
Val Ile Arg Pro Glu Thr Thr Val Glu Ala Leu Ala Thr Leu Arg Pro
    210                 215                 220
Ala Phe Asp Pro Val Asn Gly Met Val Thr Ala Gly Thr Ser Ser Ala
225                 230                 235                 240
Leu Ser Asp Gly Ala Ala Ala Met Leu Val Met Ser Glu Ser Arg Ala
                245                 250                 255
His Glu Leu Gly Leu Lys Pro Arg Ala Arg Val Arg Ser Met Ala Val
            260                 265                 270
Val Gly Cys Asp Pro Ser Ile Met Gly Tyr Gly Pro Val Pro Ala Ser
        275                 280                 285
```

```
Lys Leu Ala Leu Lys Ala Gly Leu Ser Ala Ser Asp Ile Gly Val
    290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
                340                 345                 350

Ser Thr Thr Leu Leu Asn Leu Met Glu Arg Lys Asp Val Gln Phe Gly
        355                 360                 365

Leu Ala Asp Gly Cys Val Ser Gly Leu Gly Gln Gly Ile Ala Thr Val
    370                 375                 380

Phe Glu Arg Val
385

(2) INFORMATION FOR SEQ ID NO:16:

(i) SEQUENCE CHARACTERISTICS:
        (A) LENGTH: 398 amino acids
        (B) TYPE: amino acid
        (D) TOPOLOGY: linear (ii) MOLECULE TYPE: protein (vi) ORIGINAL SOURCE:
        (A) ORGANISM: Saccharomyces uvarum (xi) SEQUENCE DESCRIPTION: SEQ ID NO:16:

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
                20                  25                  30

Ala Ala Leu Lys Gly Ala Leu Ala Lys Val Pro Glu Leu Asp Ala Ser
            35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Thr Ala Gly Leu Gly Asn
65                  70                  75                  80

His Ile Val Ala Thr Thr Val Asn Lys Val Cys Ala Ser Ala Met Lys
                85                  90                  95

Ala Ile Ile Leu Gly Ala Gln Ser Ile Lys Cys Gly Asn Ala Asp Val
                100                 105                 110

Val Val Ala Gly Gly Cys Glu Ser Met Thr Asn Ala Pro Tyr Tyr Met
            115                 120                 125

Pro Ala Ala Arg Gly Gly Ala Lys Phe Gly Gln Thr Val Leu Ile Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Asp
                165                 170                 175

Gln Gln Asp Ser Phe Ala Ile Glu Ser Tyr Gln Lys Ser Gln Gln Ser
                180                 185                 190

Gln Lys Glu Gly Lys Phe Asp Asn Glu Ile Val Pro Val Thr Ile Lys
            195                 200                 205

Gly Phe Arg Gly Lys Pro Asp Thr Gln Val Thr Asn Asp Glu Glu Pro
    210                 215                 220
```

-continued

```
Ala Arg Leu His Val Glu Lys Leu Lys Ser Ala Arg Thr Val Phe Gln
225                 230                 235                 240

Arg Glu Asn Gly Thr Val Thr Ala Ala Asn Ala Ser Pro Ile Asn Asp
                245                 250                 255

Gly Ala Ala Ala Ile Ile Leu Val Ser Glu Arg Val Leu Lys Glu Lys
                260                 265                 270

Asn Leu Lys Pro Leu Ala Ile Val Lys Gly Trp Gly Glu Ala Ala His
            275                 280                 285

Leu Pro Ala Asp Phe Thr Trp Ala Pro Ser Leu Ala Val Pro Lys Ala
290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
                340                 345                 350

Gly His Pro Leu Gly Cys Ser Gly Ala Arg Val Val Val Thr Leu Leu
                355                 360                 365

Ser Ile Leu Gln Gln Glu Gly Gly Lys Ile Gly Val Ala Ala Ile Cys
370                 375                 380

Asn Gly Gly Gly Gly Ala Ser Ser Val Val Ile Glu Lys Leu
385                 390                 395
```

(2) INFORMATION FOR SEQ ID NO:17:

(i) SEQUENCE CHARACTERISTICS:
        (A) LENGTH: 397 amino acids
        (B) TYPE: amino acid
        (D) TOPOLOGY: linear (ii) MOLECULE TYPE: protein (vi) ORIGINAL SOURCE:
        (A) ORGANISM: Rattus norvegicus (xi) SEQUENCE DESCRIPTION: SEQ ID NO:17:

```
Met Ala Leu Leu Arg Gly Val Phe Ile Val Ala Ala Lys Arg Thr Pro
1               5                   10                  15

Phe Gly Ala Tyr Gly Gly Leu Leu Lys Asp Phe Thr Ala Thr Asp Leu
                20                  25                  30

Thr Glu Phe Ala Ala Arg Ala Ala Leu Ser Ala Gly Lys Val Pro Pro
            35                  40                  45

Glu Thr Ile Asp Ser Val Ile Val Gly Asn Val Met Gln Ser Ser Ser
50                  55                  60

Asp Ala Ala Tyr Leu Ala Arg His Val Gly Leu Arg Val Gly Val Pro
65                  70                  75                  80

Thr Glu Thr Gly Ala Leu Thr Leu Asn Arg Leu Cys Gly Ser Gly Phe
                85                  90                  95

Gln Ser Ile Val Ser Gly Cys Gln Glu Ile Cys Ser Lys Asp Ala Glu
                100                 105                 110

Val Val Leu Cys Gly Gly Thr Glu Ser Met Ser Gln Ser Pro Tyr Ser
            115                 120                 125

Val Arg Asn Val Arg Phe Gly Thr Lys Phe Gly Leu Asp Leu Lys Leu
            130                 135                 140

Glu Asp Thr Leu Trp Ala Gly Leu Asp Thr Gln His Val Lys Leu Pro
145                 150                 155                 160

Met Gly Met Thr Ala Glu Asn Leu Ala Ala Gln Tyr Asn Ile Ser Arg
```

```
                    165                 170                 175
Glu Asp Cys Asp Arg Tyr Ala Leu Gln Ser Gln Gln Arg Trp Lys Ala
                180                 185                 190
Ala Asn Glu Ala Gly Tyr Phe Asn Glu Glu Met Ala Pro Ile Glu Val
            195                 200                 205
Lys Thr Lys Lys Gly Lys Gln Thr Met Gln Val Asp Glu His Ala Arg
        210                 215                 220
Pro Gln Thr Thr Leu Glu Gln Leu Gln Asn Leu Pro Pro Val Phe Lys
225                 230                 235                 240
Lys Glu Gly Thr Val Thr Ala Gly Asn Ala Ser Gly Met Ser Asp Gly
                245                 250                 255
Ala Gly Val Val Ile Ile Ala Ser Glu Asp Ala Val Lys Lys His Asn
                260                 265                 270
Phe Thr Pro Leu Ala Arg Val Val Gly Tyr Phe Val Ser Gly Cys Asp
                275                 280                 285
Pro Ala Ile Met Gly Ile Gly Pro Val Pro Ala Ile Thr Gly Ala Leu
                290                 295                 300
Lys Lys Ala Gly Leu Ser Leu Lys Asp Met Asp Leu Ile Asp Val Asn
305                 310                 315                 320
Glu Ala Phe Ala Pro Gln Phe Leu Ala Val Gln Lys Ser Leu Asp Leu
                325                 330                 335
Asp Pro Ser Lys Thr Asn Val Ser Gly Gly Ala Ile Ala Leu Gly His
                340                 345                 350
Pro Leu Gly Gly Ser Gly Ser Arg Ile Thr Ala His Leu Val His Glu
                355                 360                 365
Leu Arg Arg Arg Gly Gly Lys Tyr Ala Val Gly Ser Ala Cys Ile Gly
                370                 375                 380
Gly Gly Gln Gly Ile Ser Leu Ile Ile Gln Asn Thr Ala
385                 390                 395

(2) INFORMATION FOR SEQ ID NO:18:

(i) SEQUENCE CHARACTERISTICS:
        (A) LENGTH: 246 amino acids
        (B) TYPE: amino acid
        (D) TOPOLOGY: linear (ii) MOLECULE TYPE: protein (vi) ORIGINAL SOURCE:
         (A) ORGANISM: Alcaligenes eutrophus (xi) SEQUENCE DESCRIPTION: SEQ ID NO:18:

Met Thr Gln Arg Ile Ala Tyr Val Thr Gly Gly Met Gly Gly Ile Gly
1               5                   10                  15
Thr Ala Ile Cys Gln Arg Leu Ala Lys Asp Gly Phe Arg Val Val Ala
                20                  25                  30
Gly Cys Gly Pro Asn Ser Pro Arg Arg Glu Lys Trp Leu Glu Gln Gln
            35                  40                  45
Lys Ala Leu Gly Phe Asp Phe Ile Ala Ser Glu Gly Asn Val Ala Asp
        50                  55                  60
Trp Asp Ser Thr Lys Thr Ala Phe Asp Lys Val Lys Ser Glu Val Gly
65                  70                  75                  80
Glu Val Asp Val Leu Ile Asn Asn Ala Gly Ile Thr Arg Asp Val Val
                85                  90                  95
Phe Arg Lys Met Thr Arg Ala Asp Trp Asp Ala Val Ile Asp Thr Asn
                100                 105                 110
```

```
Leu Thr Ser Leu Phe Asn Val Thr Lys Gln Val Ile Asp Gly Met Ala
            115                 120                 125
Asp Arg Gly Trp Gly Arg Ile Val Asn Ile Ser Ser Val Asn Gly Gln
130                 135                 140
Lys Gly Gln Phe Gly Gln Thr Asn Tyr Ser Thr Ala Lys Ala Gly Leu
145                 150                 155                 160
His Gly Phe Thr Met Ala Leu Ala Gln Glu Val Ala Thr Lys Gly Val
            165                 170                 175
Thr Val Asn Thr Val Ser Pro Gly Tyr Ile Ala Thr Asp Met Val Lys
            180                 185                 190
Ala Ile Arg Gln Asp Val Leu Asp Lys Ile Val Ala Thr Ile Pro Val
            195                 200                 205
Lys Arg Leu Gly Leu Pro Glu Glu Ile Ala Ser Ile Cys Ala Trp Leu
210                 215                 220
Ser Ser Glu Glu Ser Gly Phe Ser Thr Gly Ala Asp Phe Ser Leu Asn
225                 230                 235                 240
Gly Gly Leu His Met Gly
                245

(2) INFORMATION FOR SEQ ID NO:19:

(i) SEQUENCE CHARACTERISTICS:
        (A) LENGTH: 241 amino acids
        (B) TYPE: amino acid
        (D) TOPOLOGY: linear (ii) MOLECULE TYPE: protein (vi) ORIGINAL SOURCE:
        (A) ORGANISM: Zoogloea ramigera (xi) SEQUENCE DESCRIPTION: SEQ ID NO:19:

Met Ser Arg Val Ala Leu Val Thr Gly Gly Ser Arg Gly Ile Gly Ala
1               5                   10                  15
Ala Ile Ser Ile Ala Leu Lys Ala Gly Tyr Lys Val Ala Ala Ser
            20                  25                  30
Tyr Ala Gly Asn Asp Asp Ala Ala Lys Pro Phe Lys Ala Glu Thr Gly
            35                  40                  45
Ile Ala Val Tyr Lys Trp Asp Val Ser Ser Tyr Glu Ala Cys Val Glu
50                  55                  60
Gly Ile Ala Lys Val Glu Ala Asp Leu Gly Pro Ile Asp Val Leu Val
65                  70                  75                  80
Asn Asn Ala Gly Ile Thr Lys Asp Ala Met Phe His Lys Met Thr Pro
            85                  90                  95
Asp Gln Trp Asn Ala Val Ile Asn Thr Asn Leu Thr Gly Leu Phe Asn
            100                 105                 110
Met Thr His Pro Val Trp Ser Gly Met Arg Asp Arg Ser Phe Gly Arg
            115                 120                 125
Ile Val Asn Ile Ser Ser Ile Asn Gly Gln Lys Gly Gln Met Gly Gln
            130                 135                 140
Ala Asn Tyr Ser Ala Ala Lys Ala Gly Asp Leu Gly Phe Thr Lys Ala
145                 150                 155                 160
Leu Ala Gln Glu Gly Ala Ala Lys Gly Ile Thr Val Asn Ala Ile Cys
            165                 170                 175
Pro Gly Tyr Ile Gly Thr Glu Met Val Arg Ala Ile Pro Glu Lys Val
            180                 185                 190
```

```
Leu Asn Glu Arg Ile Ile Pro Gln Ile Pro Val Gly Leu Arg Gly Glu
        195                 200                 205

Pro Asp Glu Ile Ala Arg Ile Val Val Phe Leu Ala Ser Asp Glu Ala
        210                 215                 220

Gly Phe Ile Thr Gly Ser Thr Ile Ser Ala Asn Gly Gly Gln Phe Phe
225                 230                 235                 240

Val
```

GENES FROM *CHROMATIUM VINOSUM* FOR THE PRODUCTION OF POLYHYDROXYALKANOATE

BACKGROUND OF THE INVENTION

1. Field of the Invention

This invention relates to the production of polyhydroxyalkanoate by the culture of microorganisms which produce same.

Poly-3-hydroxybutyrate is a linear polyester of D(-)-3-hydroxybutyrate. It was first discovered in *Bacillus megaterium* in 1925. Polyhydroxy-butyrate accumulates in intracellular granules of a wide variety of bacteria. The granules appear to be membrane bound and can be stained with Sudan Black dye. The polymer is produced under conditions of nutrient limitation and acts as a reserve of carbon and energy. The molecular weight of the polyhydroxybutyrate varies from around 50,000 to greater than 1,000,000, depending on the microorganisms involved, the conditions of growth, and the method employed for extraction of the polyhydroxybutyrate. Polyhydroxybutyrate is an ideal carbon reserve as it exists in the cell in a highly reduced state, (it is virtually insoluble), and exerts negligible osmotic pressure.

Polyhydroxybutyrate and related poly-hydroxyalkanoates, such as poly-3-hydroxyvalerate and poly-3-hydroxyoctanoate, are biodegradable thermo-plastics of considerable commercial importance.

The term "polyhydroxyalkanoate" as used hereinafter includes copolymers of polyhydroxy-butyrate with other polyhydroxyalkanoates such as poly-3-hydroxyvalerate.

2. Background Information

Polyhydroxyalkanoate is biodegradable and is broken down rapidly by soil microorganisms. It is thermoplastic (it melts at 180° C.) and can readily be moulded into diverse forms using technology well-established for the other thermoplastics materials such as high-density polyethylene which melts at around the same temperature (190° C.). The material is ideal for the production of biodegradable packaging which will degrade in landfill sites and sewage farms. The polymer is biocompatible, as well as biodegradable, and is well tolerated by the mammalian, including human, body, its degradation product, 3-hydroxybutyrate, is a normal mammalian metabolite. However, polyhydroxyalkanoate degrades only slowly in the body and its medical uses are limited to those applications where long term degradation is required.

Polyhydroxyalkanoate, produced by the microorganism *Alcaligenes eutrophus*, is manufactured, as a copolymer with of polyhydroxy-butyrate and polhydroxyvalerate, by Imperial Chemical Industries PLC and sold under the Trade Mark BIOPOL. It is normally supplied in the form of pellets for thermoprocessing. However, polyhydroxyalkanoate is more expensive to manufacture by existing methods than, say, polyethylene. It is, therefore, desirable that new, more economic production of polyhydroxy-alkanoate be provided.

SUMMARY OF THE INVENTION

An object of the present invention is to provide materials and a method for the efficient production of polyhydroxyalkanoate.

According to the present invention there are provided gene fragments isolated from the bacterium *Chromatium vinosum* and encoding PHA polymerase, acetoacetyl CoA reductase and β-ketothiolase.

Preferably the *C. vinosum* is of the strain designated D, available to the public from the Deutsche Sammlung fur Mikroorganismen under the Accession Number 180.

The invention also provides a 16.5 kb EcoR1 fragment of *C. vinosum* DNA, designated PP10, hybridizable to a 5.2 kb SmaI/EcoR1 fragment, designated SE52 isolated from *Alcaligenes eutrophus* and known to contain all three of said genes responsible for expression of PHAS.

The invention further provides a fragment of the said PP10 fragment, designated SE45, encoding the PHA-synthase and β-ketothiolase genes and a region, designated SB24, encoding the acetoacetyl CoA reductase gene.

The invention also provides a recombinant genome of a microorganism, preferably a bacterium or a plant, which contains one or more of said fragments designated PP10, SE45 and region SB24.

Finally, the invention provides a method for the manufacture of PHAs, comprising culturing the microorganism *Chromatium vinosum*, or a bacterium of a different species having stably incorporated within its genome by transformation one or more PHA synthesising genes from *Chromatium vinosum*.

The biosynthesis of polyhydroxyalkanoate from the substrate, acetyl-CoA involves three enzyme-catalysed steps.

The three enzymes involved are β-ketot hiolase, acetoactyl-CoA-reductase and polyhydroxy-butyrate-synthase, the genes for which have been cloned from *Chromatium vinosum*. The three genes are known to facilitate production of polyhydroxyalkanoates, the reactions involved being represented as follows:

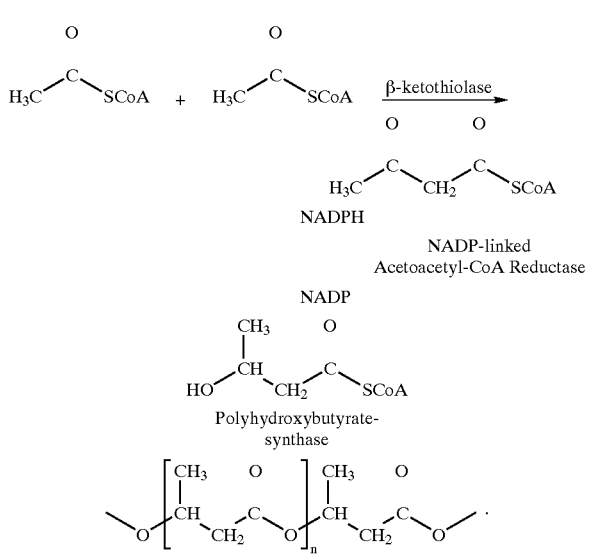

BRIEF DESCRIPTION OF THE DRAWING

The invention will now be described with reference to the accompanying drawings, of which;

FIG. 4 shows the alignment of the amino acid sequences of *Chromatium vinosum* ORF3 (SEQ ID NO:4) with PHA polymerase of *Alcaligenes eutrophus* (SEQ ID NO:5) and PHA polymerases 1 and 2 of *Pseudomonas oleovorans* (SEQ ID NO:6 and SEQ ID NO:7).

FIG. 6 shows the alignment of the amino acid sequences of ketothiolases encoded by *C. vinosum* (C.v.) (SEQ ID NO:2), *A. eutrophus* (A.e.) (SEQ ID NO:13), *Zoogloea ramigera* (Z.r) (SEQ ID NO:14), *Escherichia coli* (E.c) (SEQ ID NO:10), *Saccharomyces uvarum* (S.u) (SEQ ID NO:17) and *Rattus norvegicus* (R.n.) (SEQ ID NO:17).

FIG. 7 shows the alignment of the amino acid sequences of acetoacetyl CoA reductases encoded by *C. vinosum* (Cv) (SEQ ID NO:17), *A. eutrophus* (A.e. ) (SEQ ID NO:18) and *Z. ramigera* (Z.r.) (SEQ ID NO:18)

FIG. 8 is a Table (Table 1) showing the heterolocous expression in *Escherichia coli* of DNA fragments from *C. vinosum*. Activities of PHA biosynthetic enzymes expressed by the different fragments are shown. The levels of PHA accumulated in *E. coli* transformed with the fragments are also given.

DESCRIPTION OF THE PREFERRED EMBODIMENTS

Example

The organism *C. vinosum* was a gift from Dr J. Imhoff of the University of Bonn, Germany.

1. Isolation of DNA Fragments from *C. vinosum* Encoding PHA Synthesis Genes

A 5.2 kb SmaI/EcoRI fragment (SE52), which codes for all three PHA biosynthetic genes has previously been isolated from *Alcaligenes eutrophus* [Schubert et al., J. Bacteriol. 170 (1988)]. This fragment was used to detect PHA biosynthetic genes of *C. vinosum*. EcoRI restricted genomic DNA of *C. vinosum* was blotted on to a nylon membrane and hybridized with biotinylated SE52 DNA. One signal appeared, representing a DNA fragment of 16.5 kb.

Figure 1:
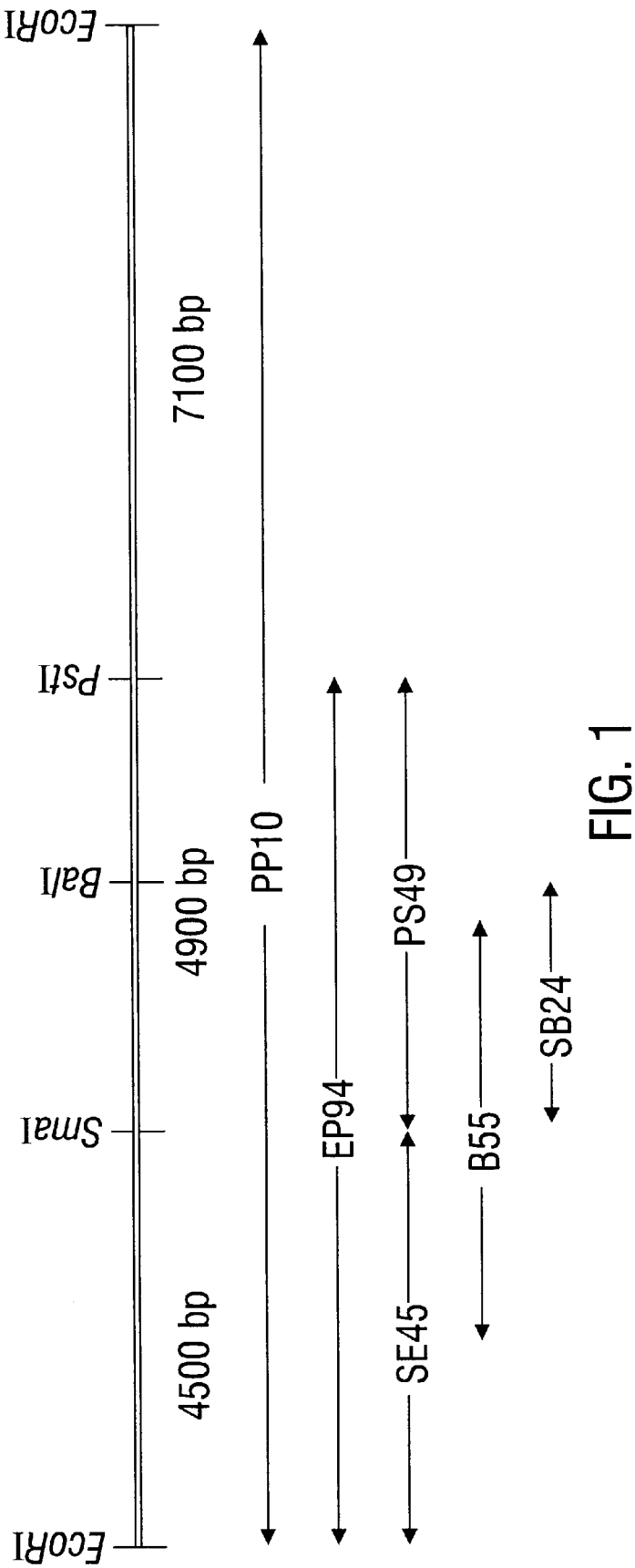
FIG. 1 is the physical map of the 16.5 kb EcoR1 fragment of *Chromatium vinosum* DNA, designated PP10. The positions of the restriction sites and positions and names of the sub-fragments are shown. PHA-synthase and β-ketothiolase genes are located in fragment SE45 and acetoacetyl CoA reductase in region SB24.

A λL47 gene bank from *C. vinosum* genomic DNA was prepared and plates with approximately 800 plaques were blotted on to nylon membranes and hybridized with biotinylated SE52 DNA. One positive recombinant phage was isolated, which harboured a 16.5 kb EcoRI fragment, which was designated PP10 (FIG. 1). With PP10 and a 9.4 kb EcoRI/PstI subfragient (EP94) of PP10, the phenotype of the wild type could be restored in PHA-negative mutants of *A. eutrophus*.

Expression studies in *E. coli* (see below) showed that a 4.5 kb SmaI/EcoRI (SE45) subfragment of EP94 encodes for PHA synthase and β-ketothiolase. The nucleotide sequence of this fragment was determined by the dideoxy-chain termination method of Sanger et al. with alkaline denatured double stranded plasmid DNA. The T7-polymerase sequencing kit of Pharmacia, Uppsala, Sweden, was used with 7-deazaguanosine-5'-tri-phosphate instead of dGTP. Most of the sequence was determined with a set of unidirectional overlapping deletion clones generated by exonuclease III digestion. For sequencing regions which were not covered by the deletion plasmids synthetic oligonucleotides were used.

Figure 2:
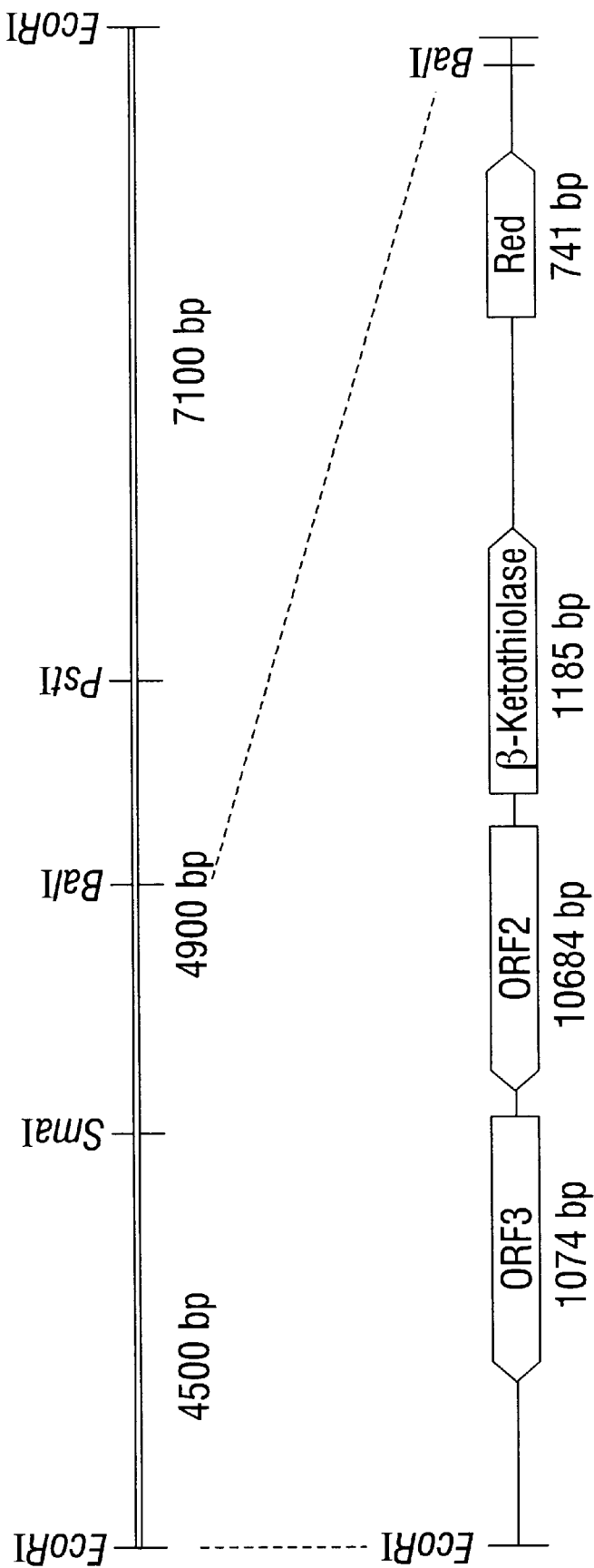
FIG. 2 is the map of PP10 showing the positions of the β-ketothiolase and acetoacetyl CoA reductase genes and of the PHA-synthase gene open reading frames ORF2 and ORF3.

It was not possible to clone the 4.9 kb SmaI/PstI fragment PS49 in a multi-copy vector. Therefore, fragment EP94 (FIG. 1) was treated with Exonuclease Bal31, ligated to Bluescript Sk and transferred to *E. coli* X1- 1 Blue. A clone was isolated which harboured Bluescript SK with a 5.5 kb fragment (B55) and which expressed β-ketothiolase and NADH-dependent reductase activity. 3146 base pairs of B55 were part of the SE45 fragment. The other part (approximately 2350 base pairs, SB24) has been sequenced applying the primer hopping strategy. The sequence and the position of the reductase gene on SB24 are known. The results of these studies, including the organisation of the PHA biosynthetic genes in *C. vinosum* and the sites of the ketothiolase, reductase and PHA synthase genes are shown in FIG. 2. The determination of the full sequence of SB24 is in progress.

2. Sequence Analysis of the *C. vinosum* PHB Synthetic Genes

Figure 3:
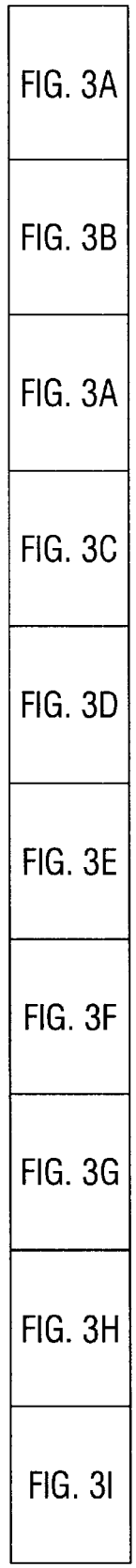
FIG. 3 is the complete nucleotide sequence of fragment SE45 (SEQ ID NO:1). The transcriptional start sites and terminators for the β-ketothiolase gene and for ORF3 and ORF2 are shown. The positions of the "−10" and "−35" sequences are also shown, as are the positions of the putative ribosome binding sites ("s/d"). Translational start and stop (*) codon are also marked and the amino acid sequences of the β-ketothiolase (SEQ ID NO:2), ORF2 (SEQ ID NO:3) and ORF3 (SEQ ID NO:4) are give.
Figure 3A:

The nucleotide sequence of SE45 is shown in FIG. 3 (SEQ ID NO:1). The fragment size of SE45 is 4506 bp.

2.1 PHB Synthase

The fragment sequence corresponding to the PHB synthase gene is designated as ORF3. The determination of synthase activity of deleted plasmids containing SE45 (See below) gave evidence that expression of ORF2 is also required for expression of synthase activity.

ORF2 and ORF3 are transcribed as an operon. The determination of the transcription start site of ORF2 was conducted by S1 nuclease mapping. This site occurs at bp 3059 from the 3' end of SE45. A putative "−10" site, given as 5'-ACAGAT-3'occurs at bp 3073–3078, and a "−35" site occurs at bp 3092–3099. A putative ribosome binding Site occurs at bp 3040–3045. The translation start codon commences at bp 3030. The translation stop codon occurs at bp 1958.

The putative ribosome binding site of ORF3 occurs at bp 1907–1911. The translation start ATG for ORF3 occurs at bp 1899, and the translation stop codon at bp 833. Putative transcriptional terminator sites occur at hairpin structures at bp 773–786 and 796–823.

ORF2 encodes, apolypypeptide of 358 amino acids with a MW of 40525 da (SEQ ID NO:5). ORF3 encodes a poly eptide of 356 amino acids with a MW of 39739 da (SEQ ID NO:4). The gene size of ORF3 is approximately 30% smaller as compared with the PHA polymerase genes of *A. eutrophus* and *P. oleovorans*. The alignments of the primary structures of *C. vinosum* PHA polymerase, *A. eutrophus* PHA polymerase and *P. oleovorans* PHA polymerases 1 and 2 are shown in FIG. 4. Thus the ORF3 *C. vinosum* polymerase is shorter than the other polymerase enzymes, lacking the first 172 amino acids from the $NH_2$ terminus of the *A. eutrophus* PRA polymerase, and the first 148 amino acids of the *Pseudomonas polymerases*. The amino acid sequence of ORF3 (SEQ ID NO:4) exhibited an overall homology of 25% to the polymerase of *A. eutrophus*, with certain discrete regions of conserved sequence.

The amino acid sequence of ORF2 (SEQ ID NO:3) showed no significant homology to other enzymes in the NBRF gene bank.

2.2 βketothiolase

The β ketothiolase and acetoacetyl CoA reductase genes are transcribed in opposite direction to ORF2 and ORF3 (FIG. 2). A "−10" site in the identified ketothiolase promoter occurs at bp 3105–3111, and a "−35"site at bp 3082–3086. A putative ribosome binding site occurs at bp 3167–3171. The translation starts signal occurs at bp 3181. The translation stop codon occurs at bp 4361.

Figure 5A:
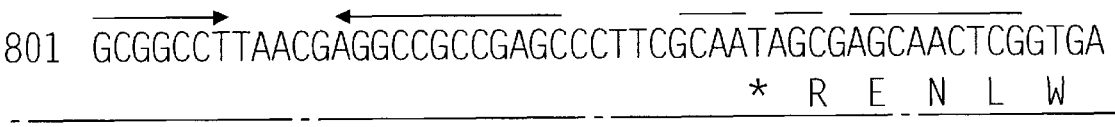
FIG. 5 shows the complete nucleotide sequence of the DNA encoding PHA synthesis genes from *Chromatium vinosum* (SEQ ID NO:8) The positions of PHA polymerase (phbC) (SEQ ID NO:4), acetoacetyl CoA reductase (phbB) (SEQ ID NO:9) and ketothiolase (phbA) (SEQ ID NO:2), genes are shown and also; the positions of ORF2 (SEQ ID NO:3), ORF4, (SEQ ID NO:10) ORF5 (SEQ ID NO:11) and ORF7 (SEQ ID NO:12).

The aligments of the primary structures of β ketothiolases from *Chromatium vinosum* and other sources are shown in FIG. 5. Considerable homology is apparent between the amino acid sequences of ketothiolases from *C. vinosum* and other bacterial and non-bacterial sources.

2.3 Acetoacetyl CoA Reductase

Figures 6, 6A, 6B, 6C, 6D:
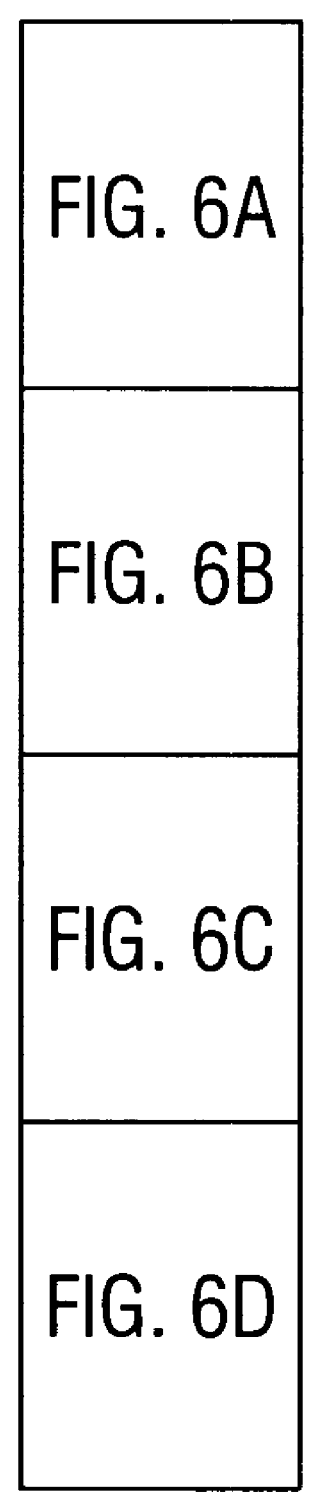

The alignments of the primary structures of acetoacetyl CoA reductases from *C. vinosum, A. eutrophus* and *z. ramigera* are shown in FIG. 6. All three reductases are of similar chain length, while considerable homology is apparent between the sequences of reductases from these bacteria.

The *Chromatium vinosum* PHA synthetic genes therefore differ from the PHA synthetic genes of *A. eutrophus* and *P. oleovorans* in the following respects:

i) Whereas *A. eutrophus* PHB polymerase, acetoacetyl CoA reductase and β ketothiolase genes are all transcribed as an operon, in *C. vinosum* the ketothiolase and reductase genes are transcribed separately from the polymerase, and are transcribed in the opposite direction to the polymerase ORF3 and ORF2 genes.

ii) In contrast to *A. eutrophus*, where one gene product is required for polymerase activity, in *C. vinosum* two gene products, represented by ORF2 and ORF3 are required for expression of polymerase activity.

iii) The *C. vinosum* ORF3 polymerase is 172 amino acids shorter, at the amino terminus, than the *A. eutrophus* polymerase, and 148 amino acids shorter than the *P. oleo-vorans* polymerases 1 and 2. The *C. vinosum* ORF3 shows only 25% homology with the primary sequence of the *A. eutrophus* polymerase.

iv) The *A. eutrophus* acetoacetyl CoA reductase enzyme involved in PHB synthesis is NADPH specific, while the *C. vinosum* enzyme exhibits a marked preference for NADH.

Between the structural genes for ketothiolase and acetoacetyl CoA reductase of *Chromatium vinosum*, two open reading frames (ORF4 (SEQ ID NO:10), and ORF5 (SEQ ID NO:11) appear, and downstream from the reductase gene an ORF7 has been identified (FIG. 5). No additional ORFs were identified in the PHA coding region of *A. eutrophus*.

3. Expression of *C. Vinosum* PHB Synthetic Genes in Other Bacteria.

With fragments PP10 and EP94 the ability to synthesise PHB could be restored to PHB negative mutants of *A. eutrophus*. Recombinant strains of the FHB negative mutant *A. eutrophus* PHB-4, transformed with these fragments, were able to synthesise polymers containing 3-hydroxybutyrate and 3-hydroxyisovalerate at significant proportions, when supplied with appropriate substrates.

Studies on expression of *C. vinosum* DNA fragments in *E. coli* are presented in Table 1. Thus *E. coli* transformed with plasmids containing fragments PP10 and EP94 expressed PHB polymerase, acetoacetyl CoA reductase and β ketothiolase activities. They also synthesised PHB up to between 10 and 12% dry weight. *E. coli* transformed with plasmids containing fragment SE45 expressed PHB polymerase and β ketothiolase, but not acetoacetyl CoA reductase, and were unable to synthesise PHB.

4. Polymer Biochemistry

The specific optical rotations of methyl 3-hydroxybutyric acid liberated by methanolysis of PHB from *C. vinosum* (accumulated from acetate), from *A. eutrophus* PHB-4 pHP1014:PP10 (accumulated from fructose) and *E. coli* S17-1 pSUP202:PP10 (accumulated from glucose) were all negative. The determined values of the specific optical rotation were similar to those for PHB isolated from *A. eutrophus* (accumulated from fructose).

What is claimed is:

1. A 16.5 kb EcoR1 fragment of *Chromatium vinosum* DNA hybridizable to a 5.2 kb SmaI/EcoR1 fragment, designated SE52 isolated from Alcaligenes eutrophus and known to contain the genes encoding PHA-synthase acetoacetyl CoA reductase and β-ketothiolase genes.

2. A fragment of the DNA claimed in claim 1 comprising SEQ ID NO: 1, encoding the PHA-synthase and β-ketothiolase genes.

3. A SmaI/BalI fragment of the DNA claimed in claim 1, encoding the acetoacetyl CoA reductase gene.

4. An isolated gene, encoding β-ketothiolase, having the nucleotide sequence shown in FIG. 3 (SEQ ID NO:1).

5. An isolated gene encoding polyhydroxyalkanoate synthase (phbC), comprised in the nucleotide sequence shown in FIG. 5 (SEQ ID NO:8).

6. An isolated gene encoding acetoacetyl CoA reductase (phbB) comprised in the nucleotide sequence shown in FIG. 5 (SEQ ID NO:8).

7. A DNA fragment isolated from a 16.5 kb EcoR1 fragment of the bacterium *Chromatium vinosum*, said fragment encoding at least one enzyme selected from the group consisting of polyhydroxyalkanoate (PHA) synthase, acetoacetyl CoA reductase and β-ketothiolase.

8. The DNA fragment of claim 7 which encodes polyhydroxyalkanoate (PHA) synthase, acetoacetyl CoA reductase and β-ketothiolase.

9. A vector comprising a fragment as claimed in claim 7.

10. A bacterium having incorporated into its genome one or more fragments as claimed in claim 7, said fragments being heterologous fragments.

11. A plant having stably incorporated in its genome by transformation one or more fragments as claimed in claim 7.

12. A method for the manufacture of polyhydroxyalkanoates, comprising culturing a recombinant bacterium having stably incorporated within its genome by transformation a DNA fragment according to claim 8.

13. An isolated DNA sequence comprising ORF2 of the *Chromatium vinosum* PHA synthase gene.

14. An isolated DNA sequence comprising ORF3 of the *Chromatium vinosum* PHA synthase gene.

15. A DNA fragment as claimed in claim 7 in which the *Chromatium vinosum* is of the strain, available to the public from the Deutsche Sammlung für Mikroorganismen under the Accession Number 180.

* * * * *